(12) United States Patent
Kondrup et al.

(10) Patent No.: US 9,808,228 B2
(45) Date of Patent: Nov. 7, 2017

(54) TISSUE DEBRIS AND BLOOD COLLECTION DEVICE AND METHODS OF USE THEREOF

(71) Applicant: Laparoscopic Innovations LLC, Milford, DE (US)

(72) Inventors: James Dana Kondrup, Binghamton, NY (US); Brenda A. Sylvester, Binghamton, NY (US); Michelle Lee Branning, Binghamton, NY (US)

(73) Assignee: Laparoscopic Innovations, LLC, Milford, DE (US)

( * ) Notice: Subject to any disclaimer, the term of this patent is extended or adjusted under 35 U.S.C. 154(b) by 99 days.

(21) Appl. No.: 14/669,278

(22) Filed: Mar. 26, 2015

(65) Prior Publication Data

US 2015/0272561 A1    Oct. 1, 2015

Related U.S. Application Data

(60) Provisional application No. 61/967,805, filed on Mar. 26, 2014.

(51) Int. Cl.
| | |
|---|---|
| *A61B 17/24* | (2006.01) |
| *A61B 17/00* | (2006.01) |
| *A61B 17/42* | (2006.01) |
| *A61B 17/32* | (2006.01) |
| *A61B 90/00* | (2016.01) |

(52) U.S. Cl.
CPC ........ *A61B 17/00234* (2013.01); *A61B 17/42* (2013.01); *A61B 2017/00287* (2013.01); *A61B 2017/320024* (2013.01); *A61B 2090/3937* (2016.02)

(58) Field of Classification Search
CPC ......... A61B 17/00; A61B 17/42; A61B 17/24; A61B 17/00234; A61B 19/00; A61B 19/54
See application file for complete search history.

(56) References Cited

U.S. PATENT DOCUMENTS

2013/0184536 A1*   7/2013   Shibley ............ A61B 17/00234
                                                        600/235

* cited by examiner

*Primary Examiner* — Victor Nguyen
(74) *Attorney, Agent, or Firm* — Stradley Ronon Stevens & Young, LLP

(57) ABSTRACT

Protective barrier for laparoscopy. The barrier has a closed bottom, wall(s), and open end. The barrier may incorporate a drawstring and/or optional flexible stay(s), in internal channel around periphery of the open end of bag. The barrier may optionally utilize self-sealing communication in closed bottom. Furthermore, barrier may also include flexible ring or other shapes positioned inside and tube passing through communication in the closed bottom. Protective barrier is configured to be collapsed, rolled, and/or folded into a size that can pass through an opening, such as a trocar. Protective barrier, when deployed in the peritoneal cavity, may be used to collect tissue, tissue parts, blood and/or other fluid that may spray during Morcellation or other laparoscopic procedure. After completion of the procedure, protective barrier can be collapsed, rolled or folded at a size that can be easily removed from the peritoneal cavity.

6 Claims, 23 Drawing Sheets

TISSUE DEBRIS AND BLOOD COLLECTION DEVICE AND METHODS OF USE THEREOF

CROSS-REFERENCE TO RELATED APPLICATION

This application claims the priority and benefit of U.S. Provisional Patent Application Ser. No. 61/967,805, titled "Tissue Debris and Blood Collection Device and Methods of Use Thereof," filed on Mar. 26, 2014, the entirety of which is incorporated herein by reference.

FIELD OF THE INVENTION

The present invention generally relates to improvements to laparoscopic and other minimally invasive surgical procedures in humans or animals including by way of non-limiting example Morcellation, as well as a collection device used in connection therewith.

BACKGROUND OF THE INVENTION

Gynecologic as well as general surgeons continue to increase the number of surgeries that are being performed by minimally-invasive procedures. These procedures often involve laparoscopy through small holes in the abdominal wall. Laparoscopy faces new challenges such as determining methods for removing large organ or tissue specimens through small holes in the abdomen.

To address these challenges, the medical industry has developed many different types of tissue morcellator devices to remove the tissue specimens in a "cut up" or morcellated strip type fashion from the peritoneal cavity or elsewhere from within the body. Furthermore, some surgeons have performed "hand Morcellation" as another laparoscopic procedures in which tissue in the peritoneal cavity, or elsewhere in the body, is cut by hand into small pieces using cutting devices passed through a slightly larger hole and later removed through the hole. Morcellation procedures are usually accomplished with little, if any, regard to the control, identification, and removal of tissue fragments and/or blood that is dropped or sprayed internally within the peritoneal cavity of a patient during a procedure. If any attention is paid to dropped or sprayed tissue, only larger, macroscopic fragments may be retrieved and removed from the patient.

Recently, a Morcellation procedures, often referred to as "open power Morcellation," has come under extreme criticism in the medical community. During "open power Morcellation" while performing a hysterectomy (partial, total, radical), myomectomy (to remove fibroids), or other procedure to remove cancerous or noncancerous tissue from the uterus, it is commonplace for pieces of uterine tissue and blood to be sprayed about and dropped into the peritoneal cavity. Some patients who have undergone this procedure have developed benign and metastatic fragment disease as reported in the medical literature. In responding to this significant problem, several private and government entities have moved to prohibit or restrict "open power Morcellation." This will unfortunately diminish significant advances in the field of minimally-invasive laparoscopic surgery for women and in other surgical applications as well.

Accordingly, there is a need for a technique and device for collecting and assisting in removing tissue and blood that may be sprayed or may fall into the peritoneal cavity during a Morcellation procedure. At present, no products on the market address this need. There are bags designed for other purposes, but these bags are inadequate for addressing the present need for several reasons. For example, retrieval bags are attached to a frame or are either too small or fail to stay open or maintain their shape to be effective during a Morcellation procedure.

Therefore, there is a need for new techniques and collection devices to address the problems with current Morcellation procedures. This invention addresses the problems without regressing from the advancements made in this area of surgical medicine. The invention, which may be referred to generally as "Endo-Field," represents a field in which surgeons can continue to operate laparoscopically and minimize, if not prevent, unwanted dissemination of blood and piece(s) of tissue throughout the peritoneal cavity by collecting and removing such blood and piece(s) of tissue during the Morcellation procedure.

BRIEF DESCRIPTION OF THE FIGURES/VIDEOS

BRIEF DESCRIPTION OF THE INVENTION

Figure 1:
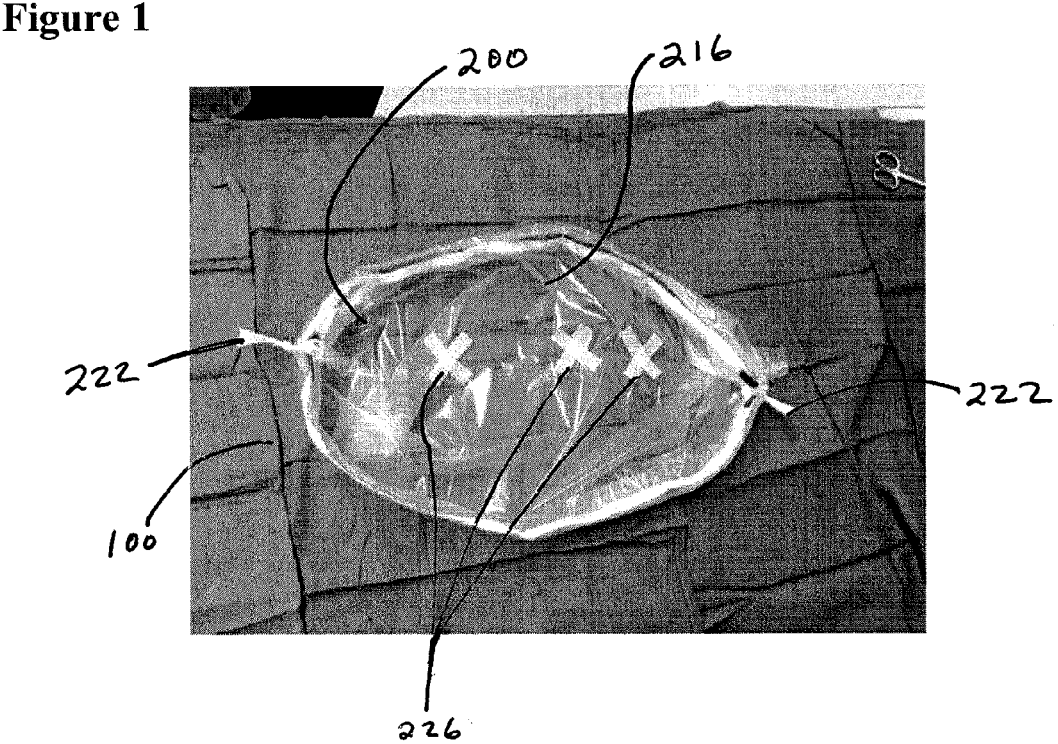
FIG. 1 shows an embodiment of the Endo-Field collection device of the present invention.
Figure 2:
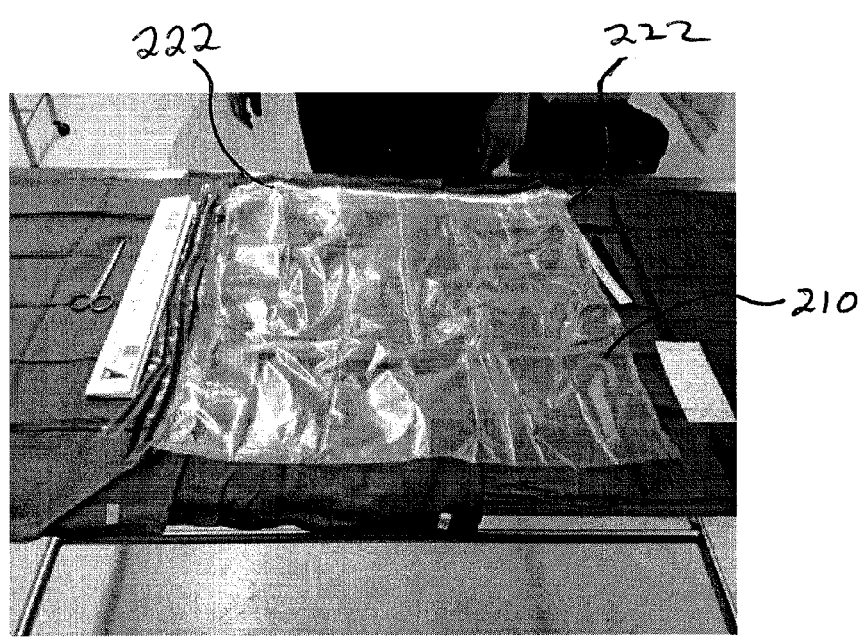
FIG. 2 shows an entire bag having a closed end and an opened end prior to assembly into the Endo-Field collection device.
Figures 3A, 3B:
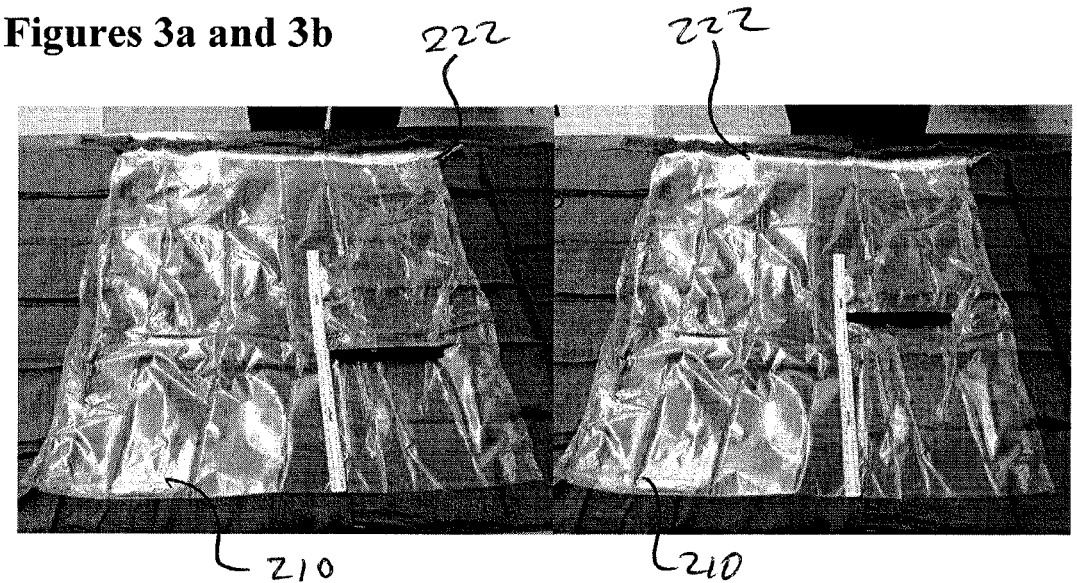
FIGS. 3a and 3b show the entire bag being measured to size.
Figure 4:
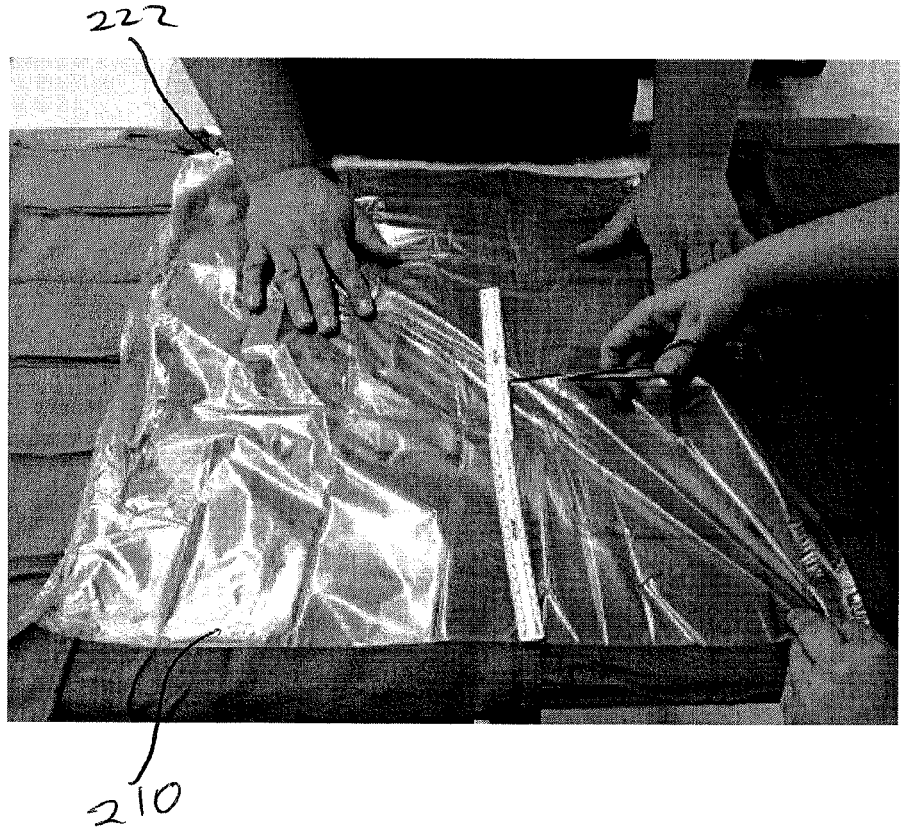
FIG. 4 shows the measured entire bag being cut to size.
Figure 5:
FIG. 5 shows the drawstrings being removed from the upper sleeve like portion of the bag that was cut away.
Figure 6:
FIG. 6 shows the portion of the bag with the closed end that has been cut, as well as the drawstrings previously removed from the full bag.
Figure 7:
FIG. 7 shows placement of the drawstrings around the open end of the cut portion of the bag having the closed end.
Figure 8:
FIG. 8 shows the cut portion of the bag being cut along its upper open end.
Figure 9:
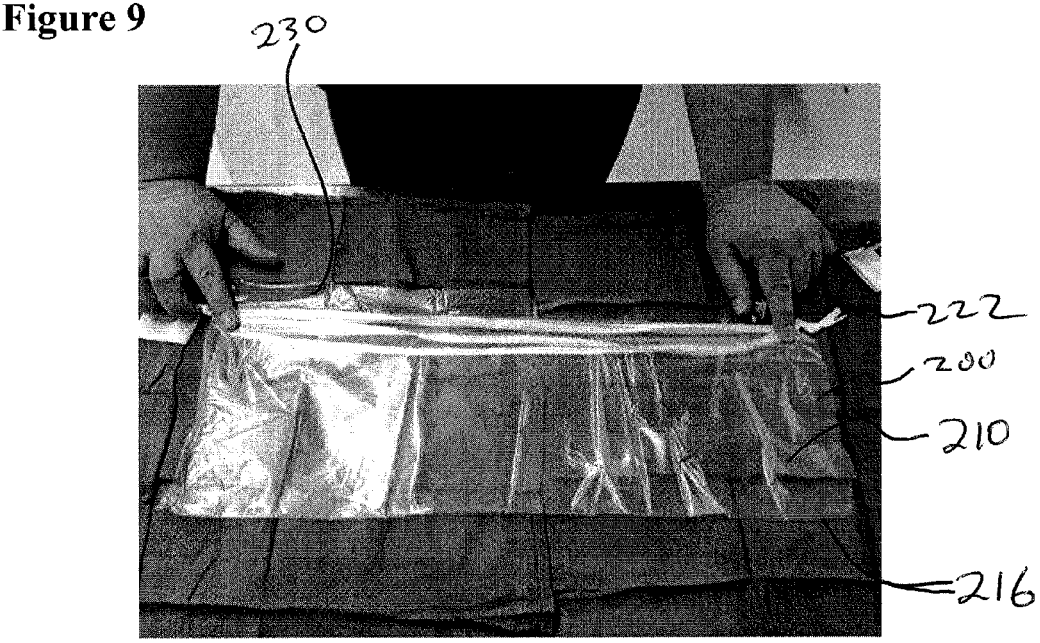
FIG. 9 shows the cut portions of the upper open end of the bag being folded over the drawstrings positioned around the upper portion of the bag.
Figure 10:
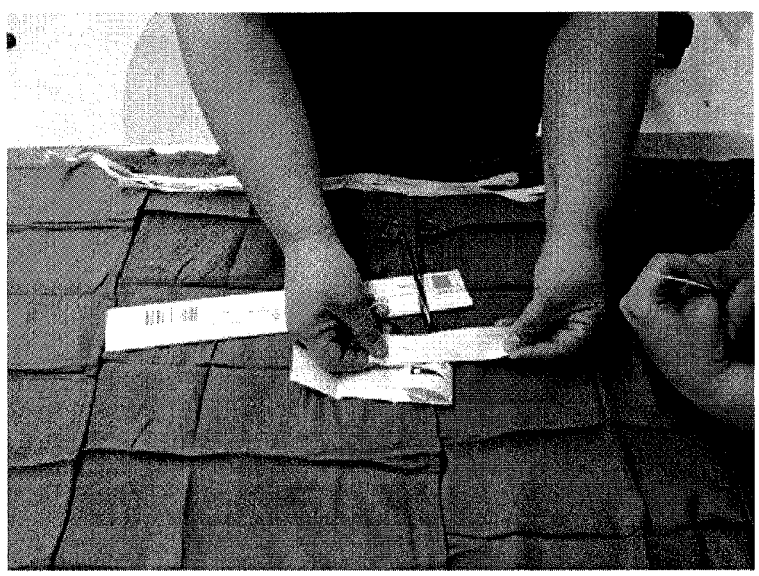
FIG. 10 shows adhesive film (Steri-drape) being cut in preparation to create a channel for the drawstring by sealing the folded-over, upper end of the bag to the external side wall of the bag.
Figure 11:
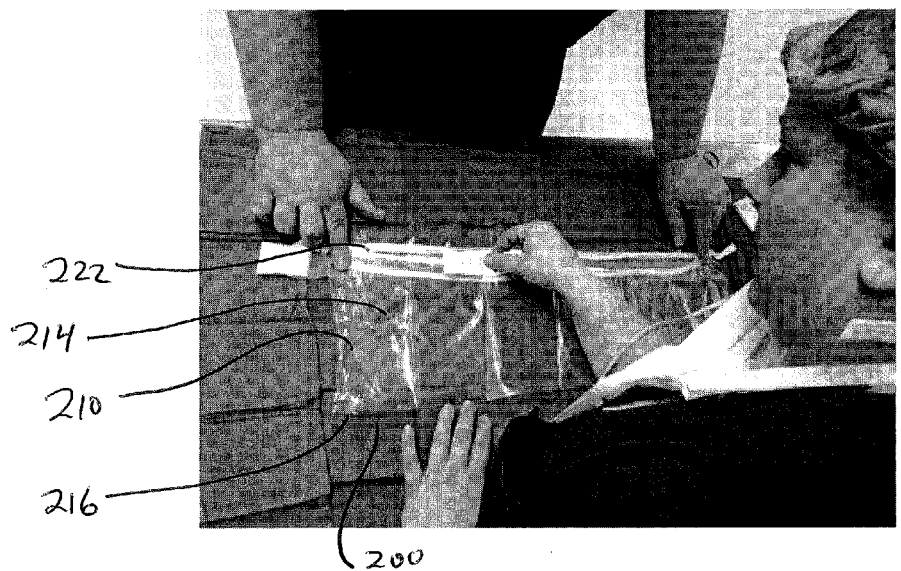
FIGS. 11, 12 and 13 show the application of the adhesive film to the bag to form the channel for the drawstring.
Figure 12:
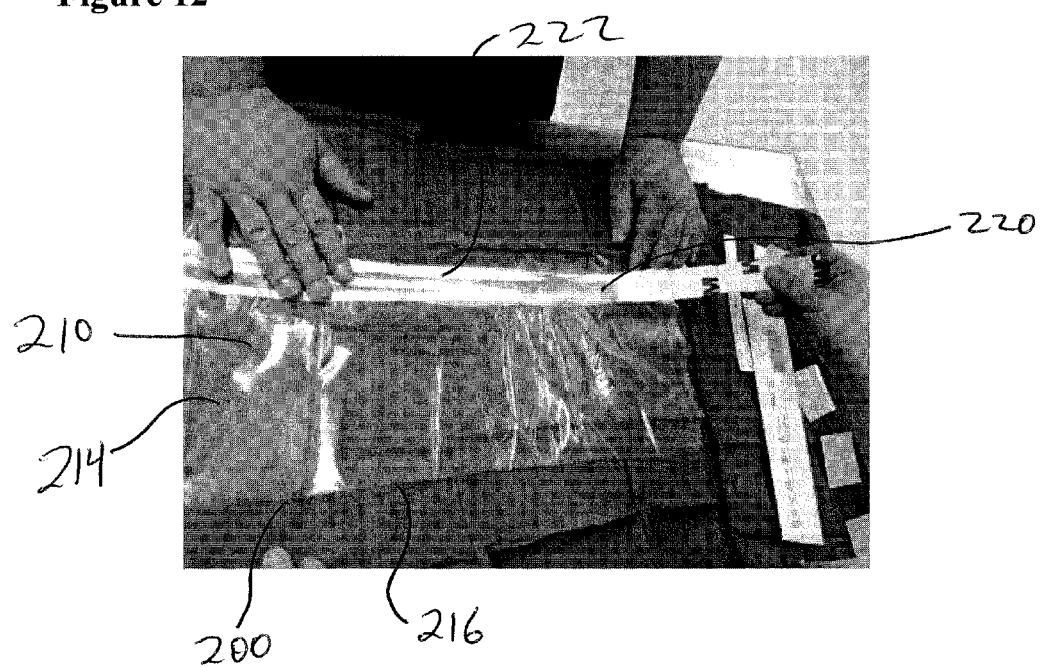
Figure 13:
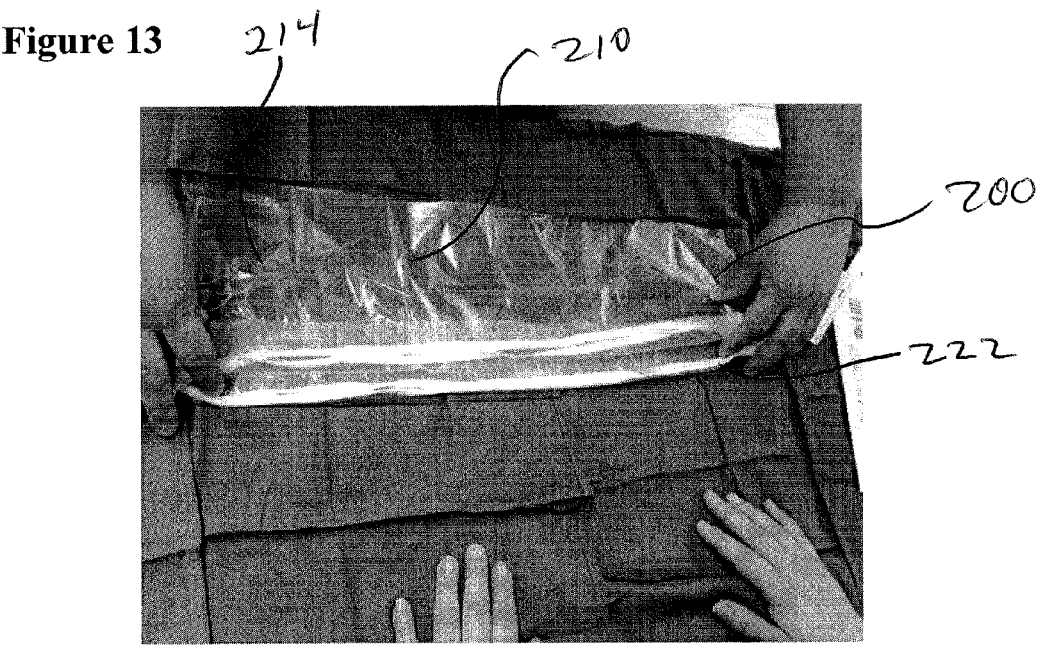
Figure 14:
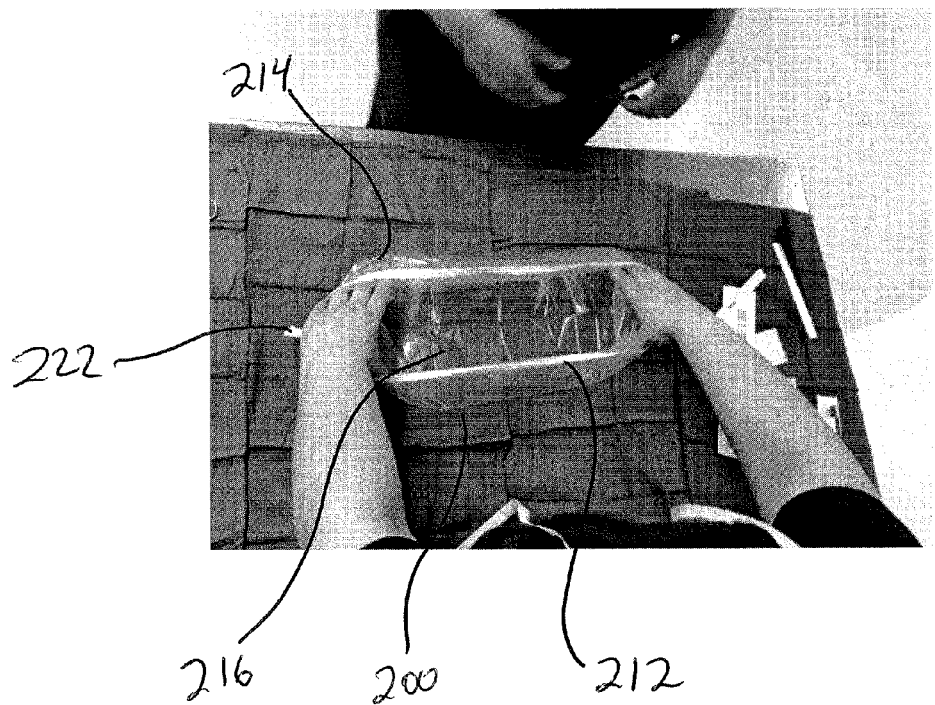
FIG. 14 shows the bag with the drawstring positioned in the channel.
Figures 15A, 15B:
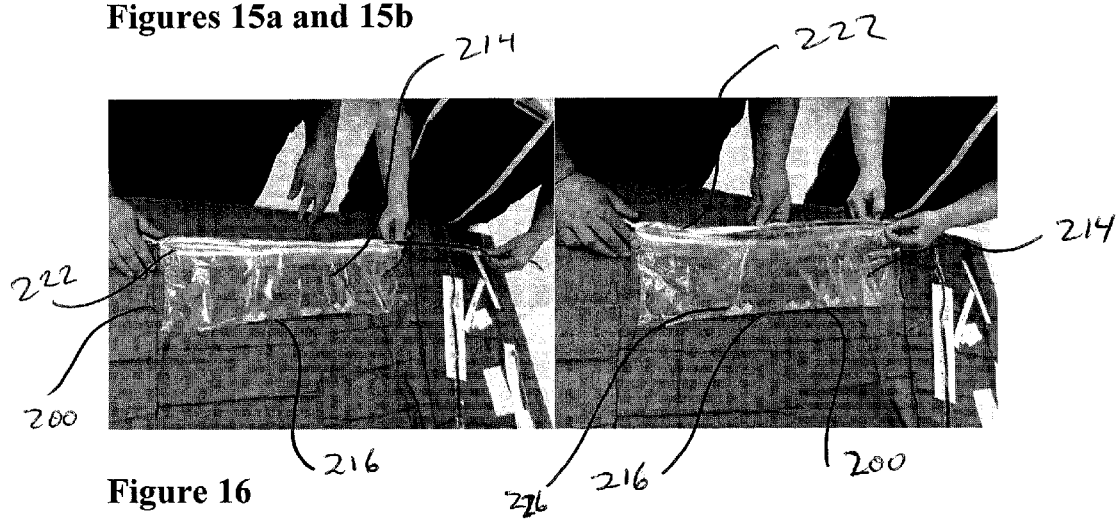
FIGS. 15a, 15b, 16, 17, 18 and 19 show an alternative embodiment wherein malleable rails are inserted into a channel formed with adhesive film that seals overlapping upper flaps to side walls of the bag.
Figure 16:
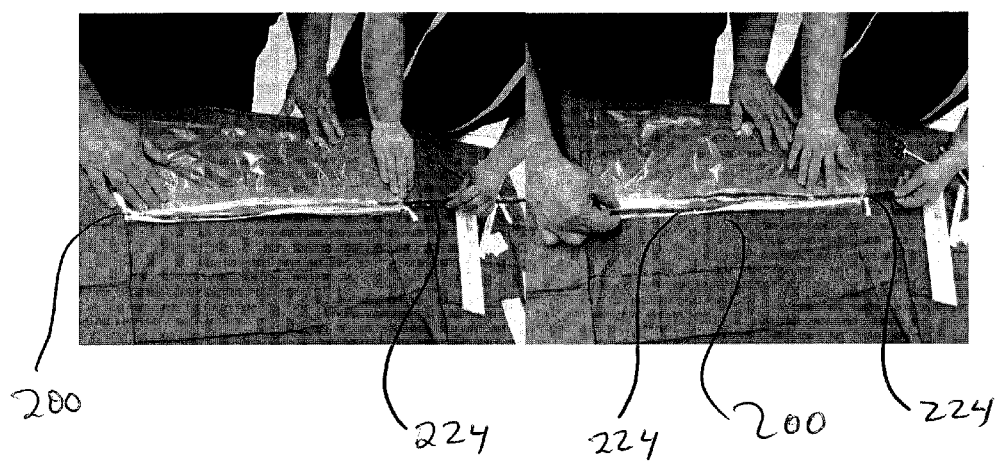
Figure 17:
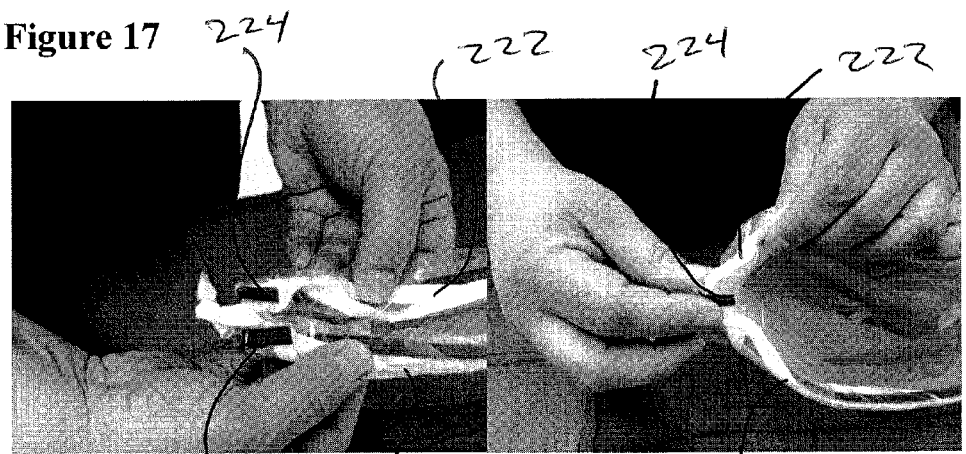
Figure 18:
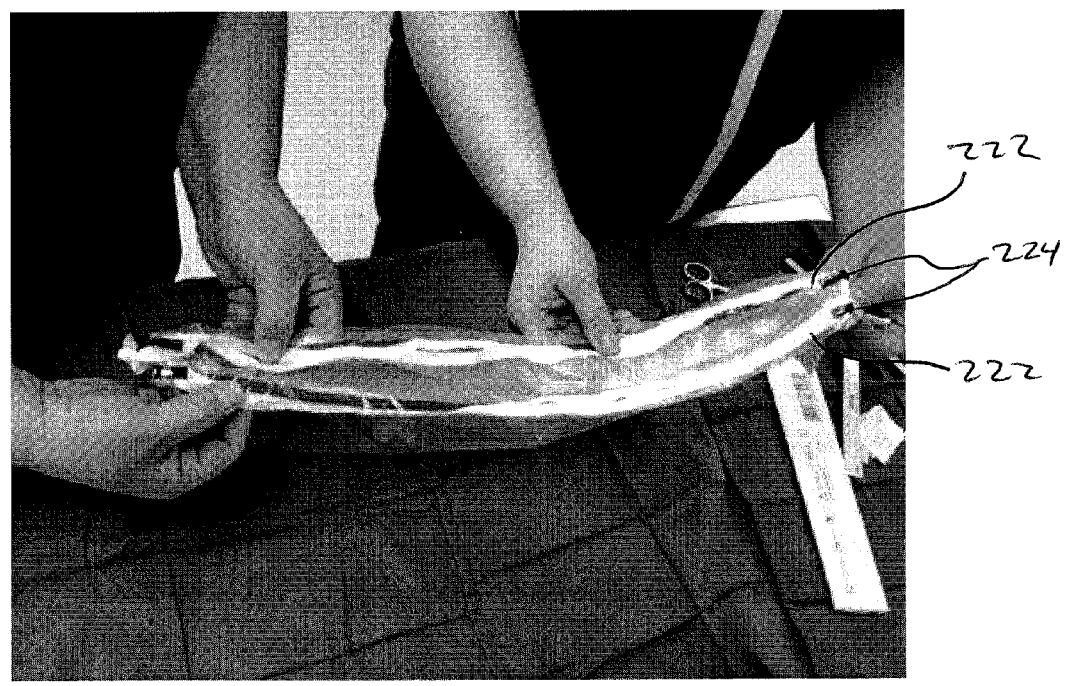
Figure 19:
Figure 20:
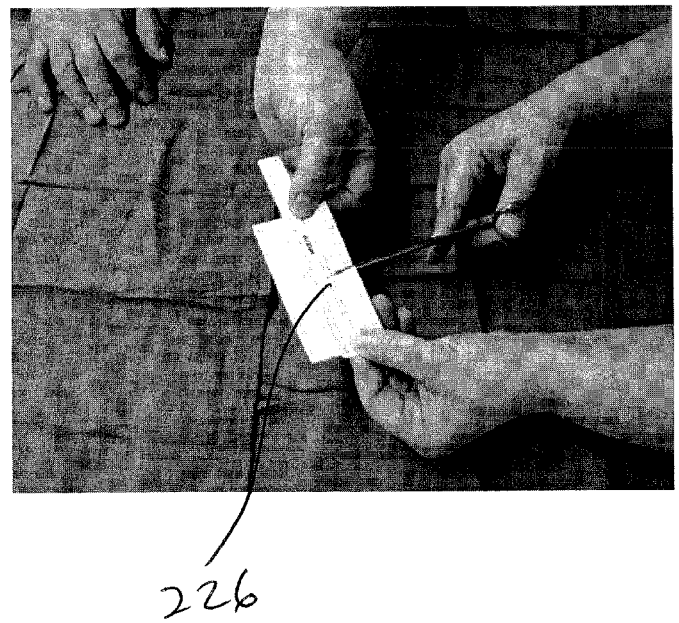
FIGS. 20, 21, 22, 23 and 24 show marking strips being cut and placed in the bottom of the Endo-Field collection device, as well as anchor tabs along the open end of the device (FIG. 24).
Figure 21:
Figure 22:
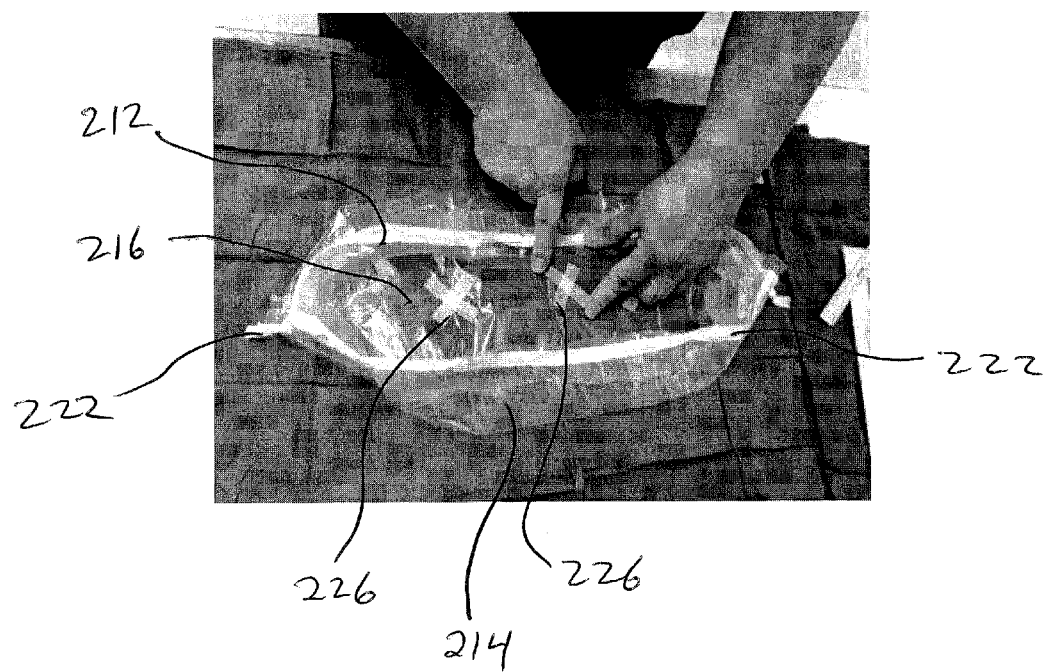
Figure 23:
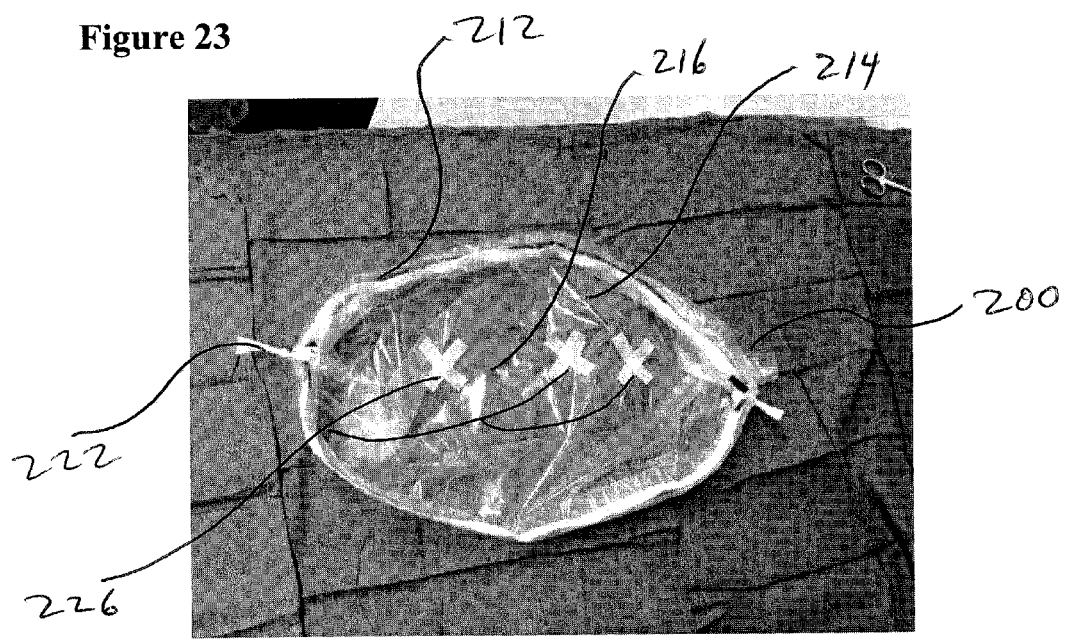
Figure 24:
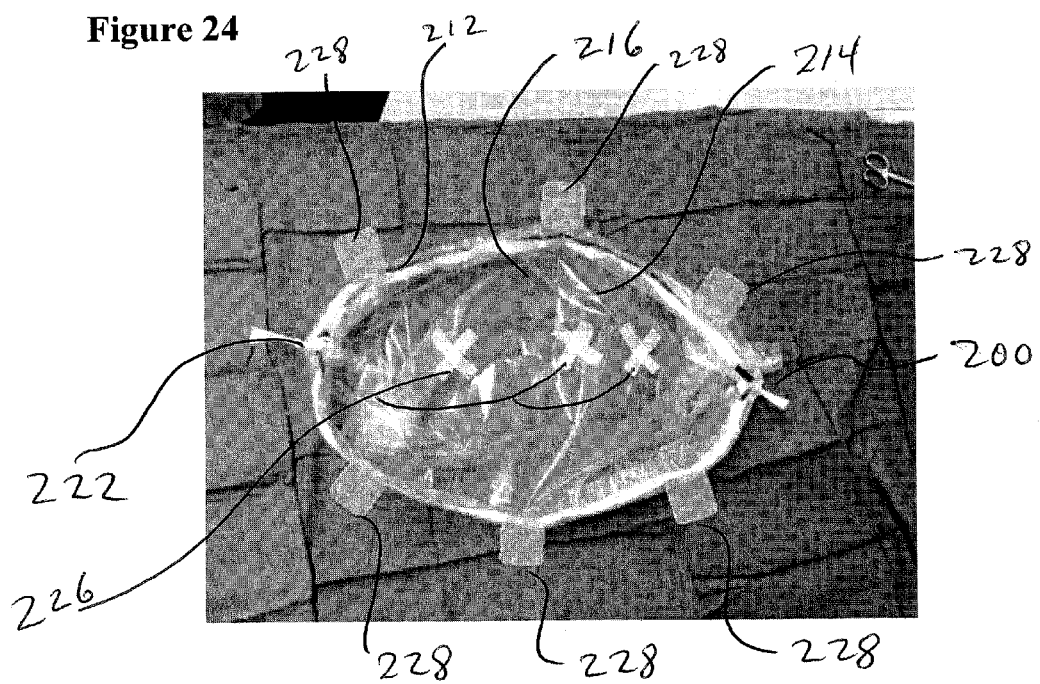
Figure 25:
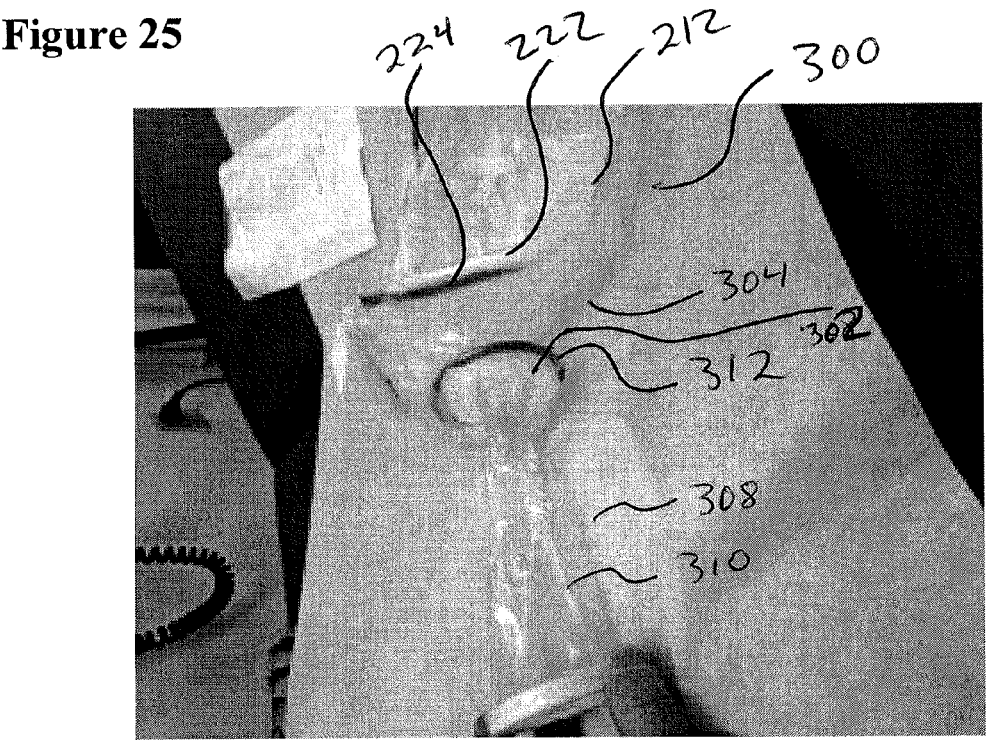
FIG. 25 shows another embodiment of the transvaginal Endo-Field collection device of the present invention.
Figure 26:
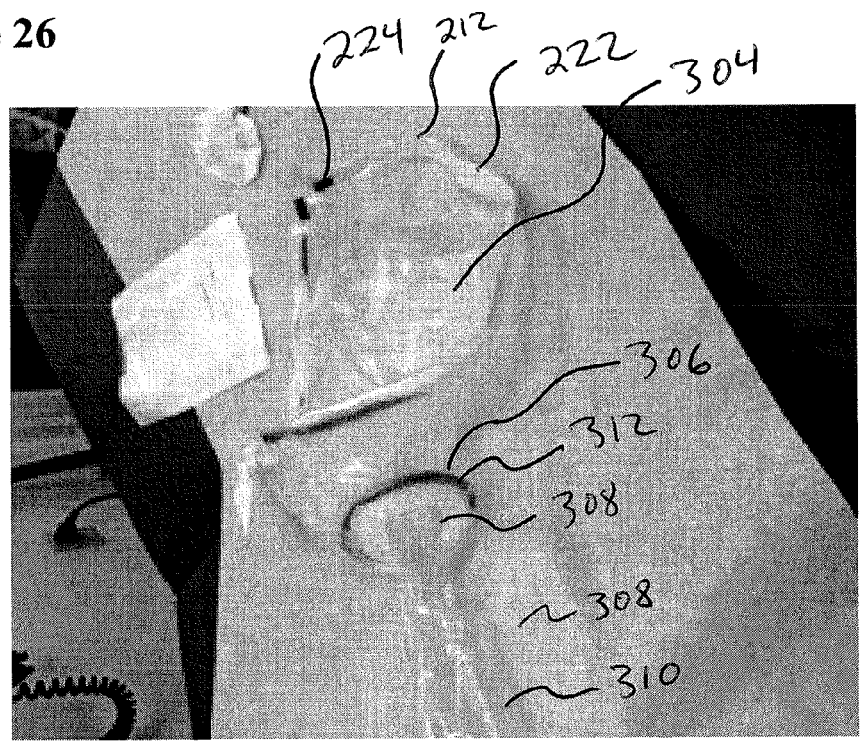
FIG. 26 shows another view of the collection device of FIG. 25.
Figure 27:
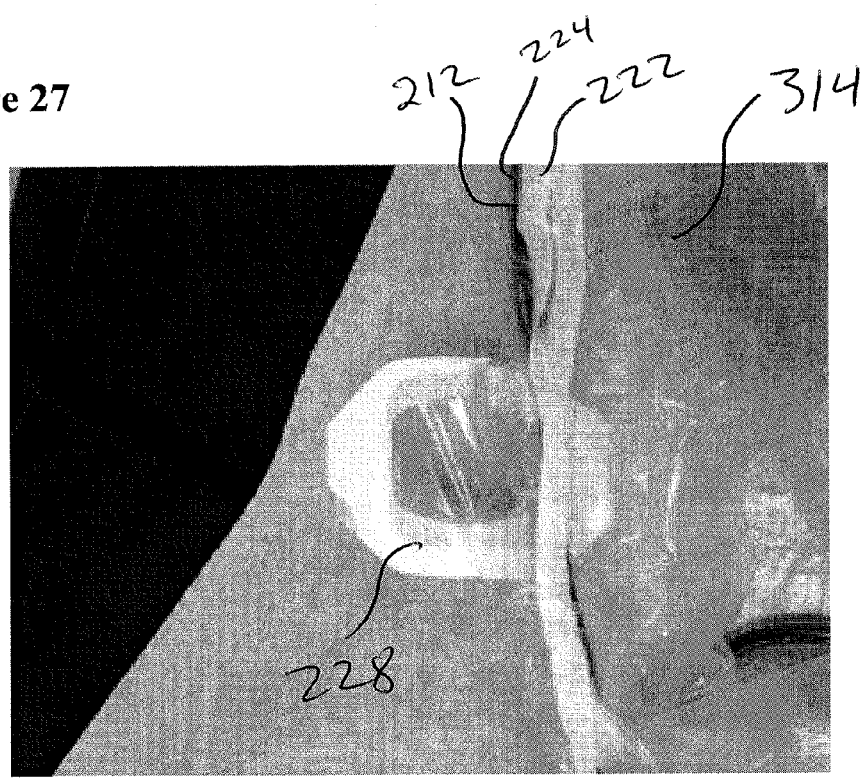
FIGS. 27, 28 and 29 show anchor tabs affixed along the open end of the collection device of FIG. 25.
Figure 28:
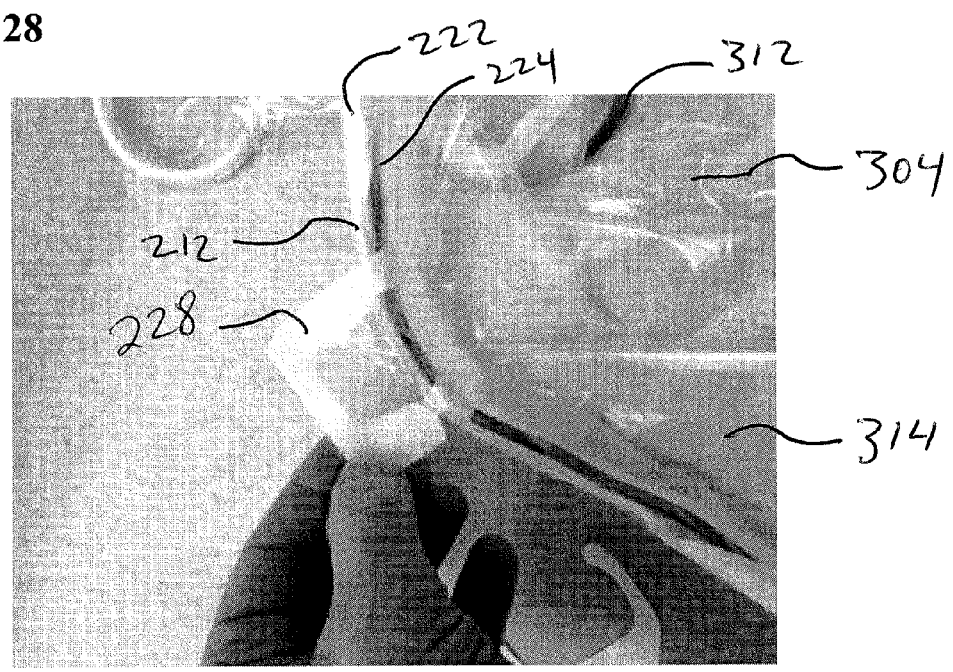
Figure 29:
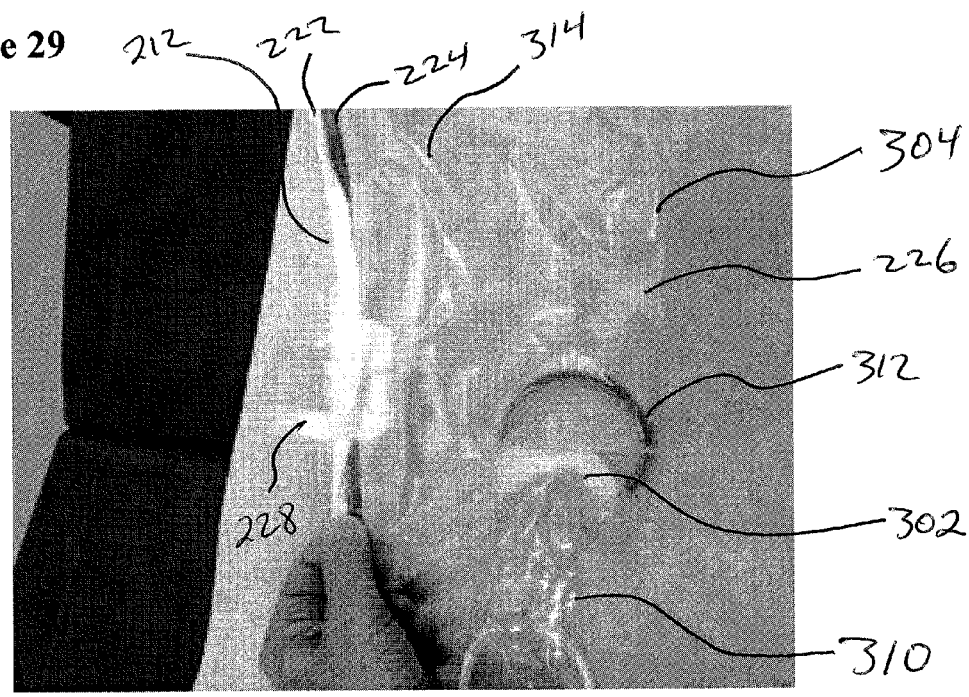
Figure 30:
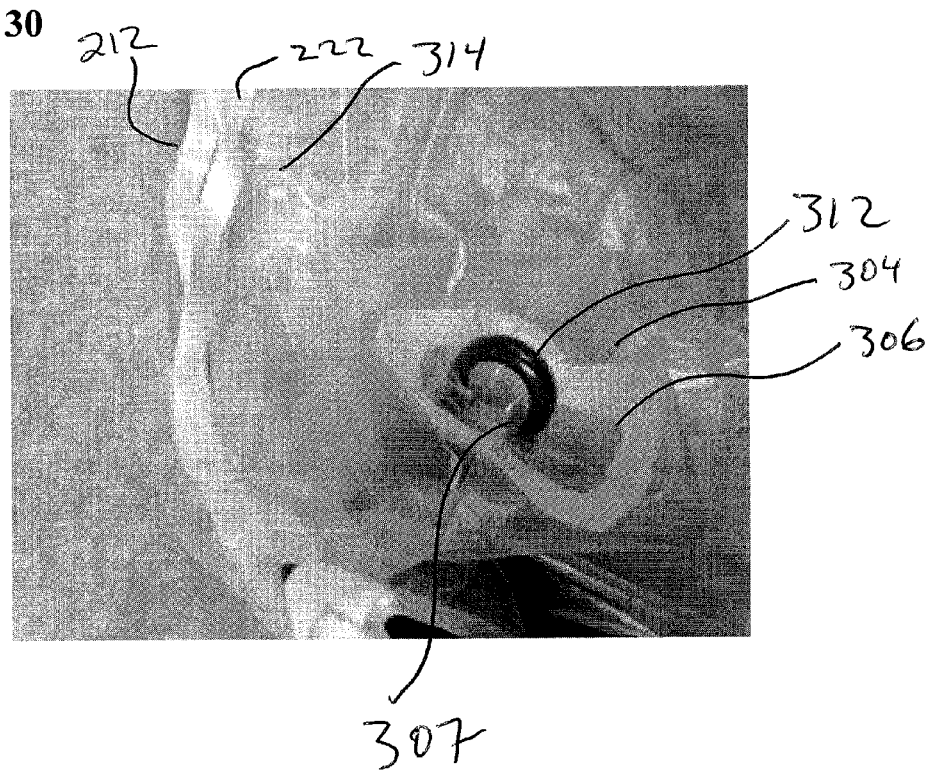
FIGS. 30, 31, 32, 33 and 34 show the flexible ring being inserted through a communication in the bottom of the collection device and positioned in the collection device to secure the sheath-like surgical communication to the collection bag.
Figure 31:
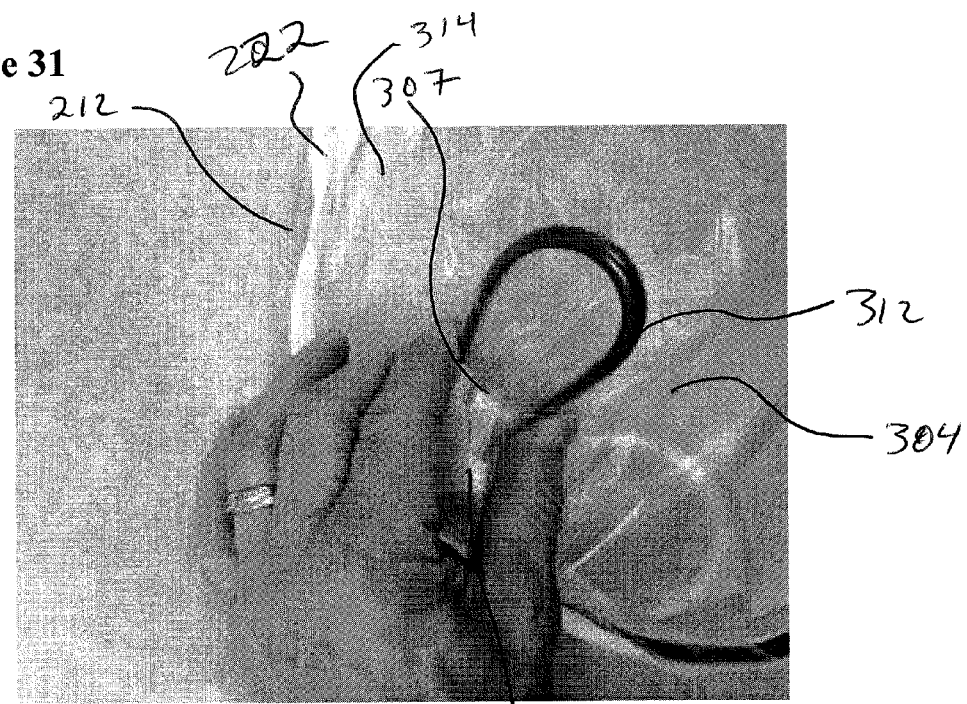
Figure 32:
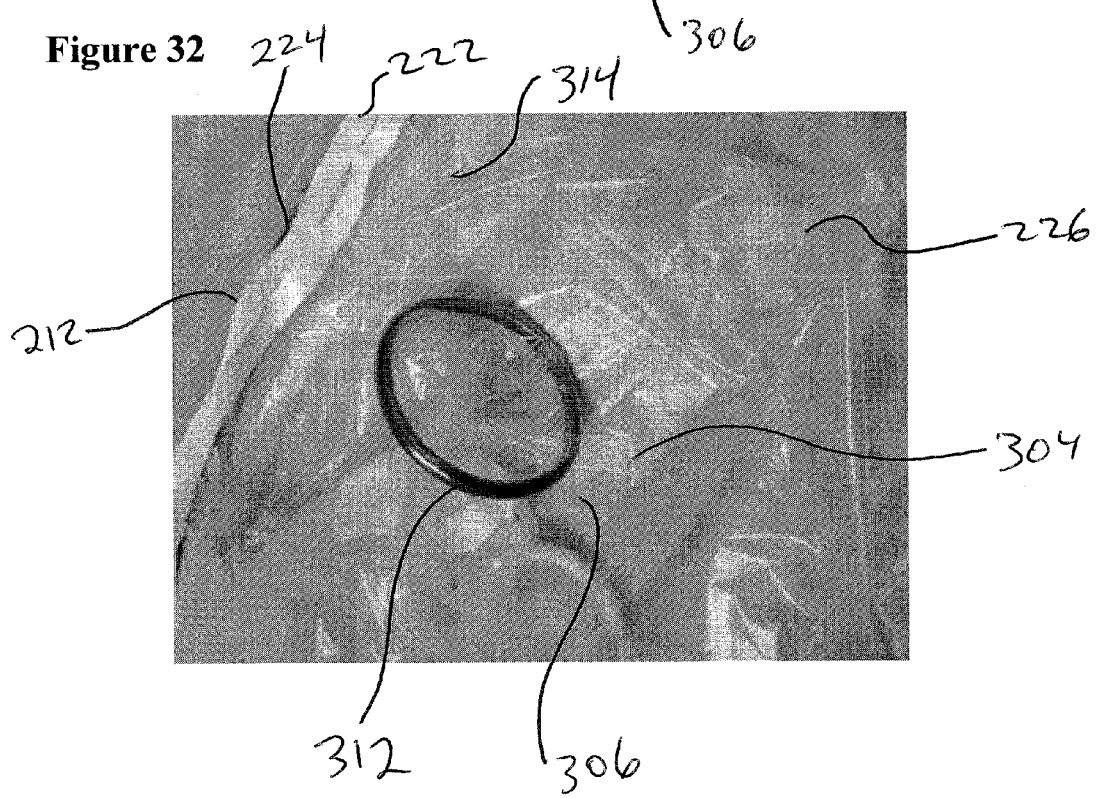
Figure 33:
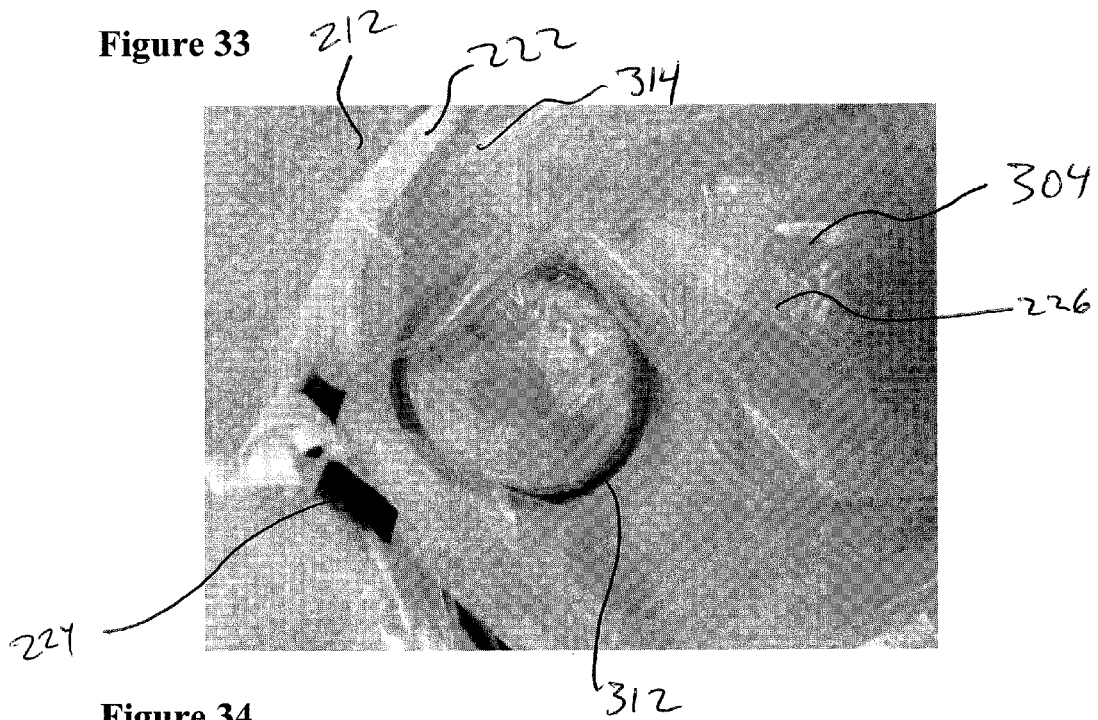
Figure 34:
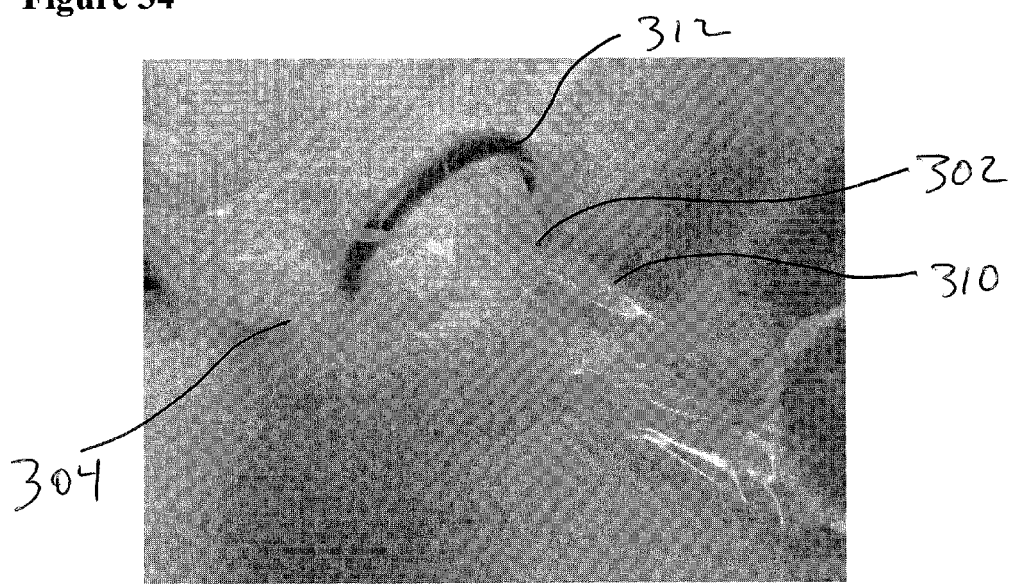
Figure 35:
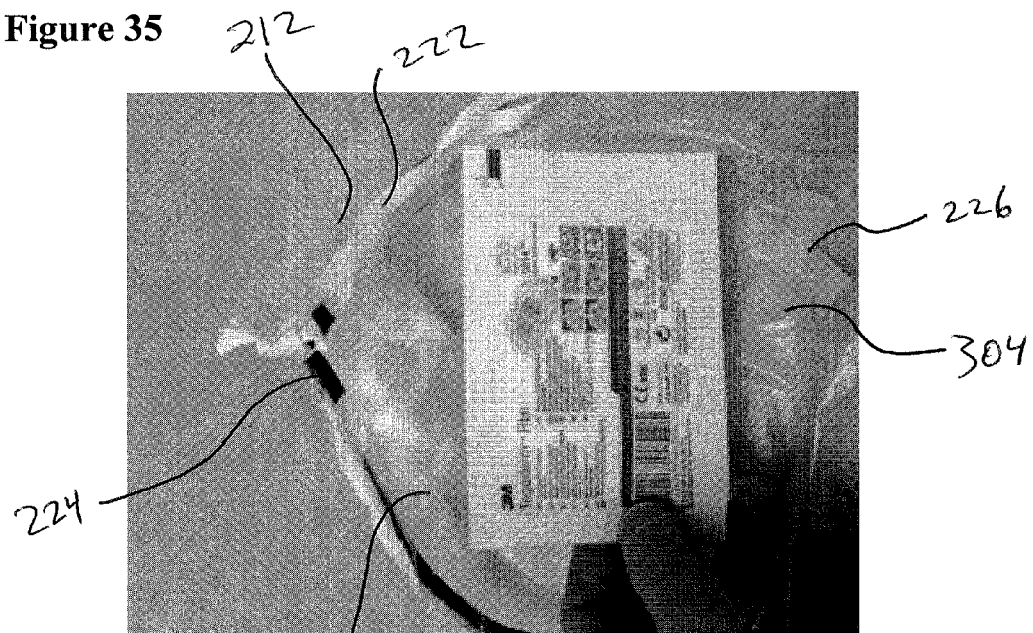
FIGS. 35, 36, 37, 38 and 39 show the placement of an adhesive sealing film on the bottom of the collection bag, as well as the communication provided through the film to receive the sheath-like surgical communication.
Figure 36:
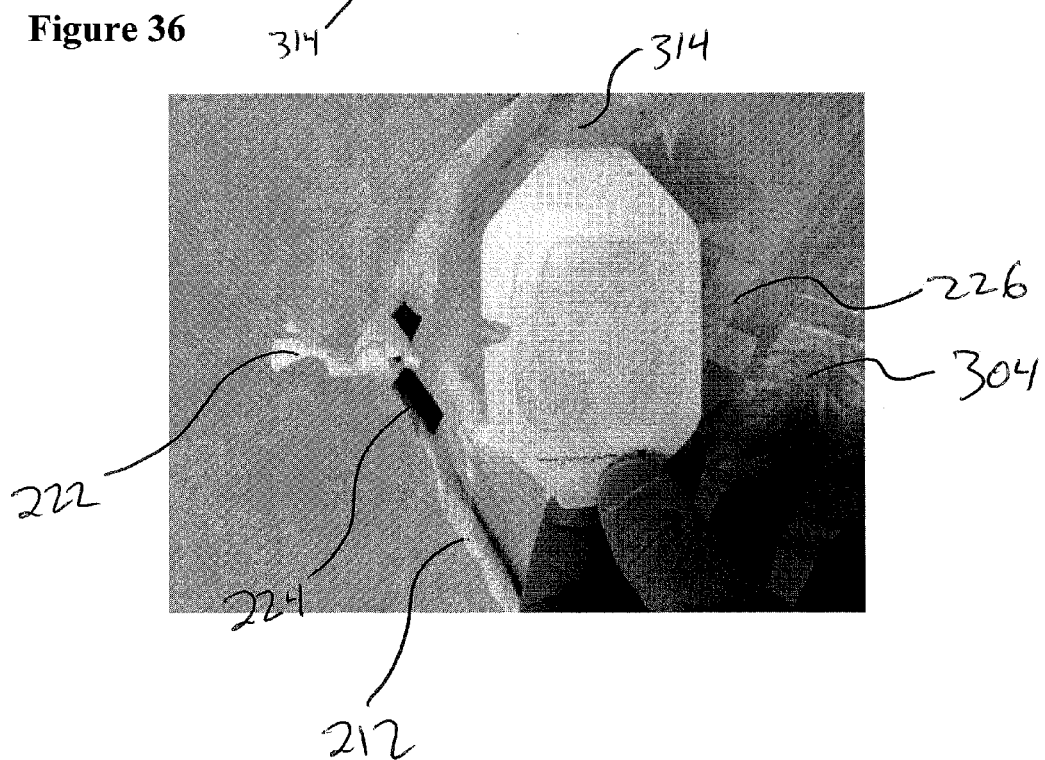
Figure 37:
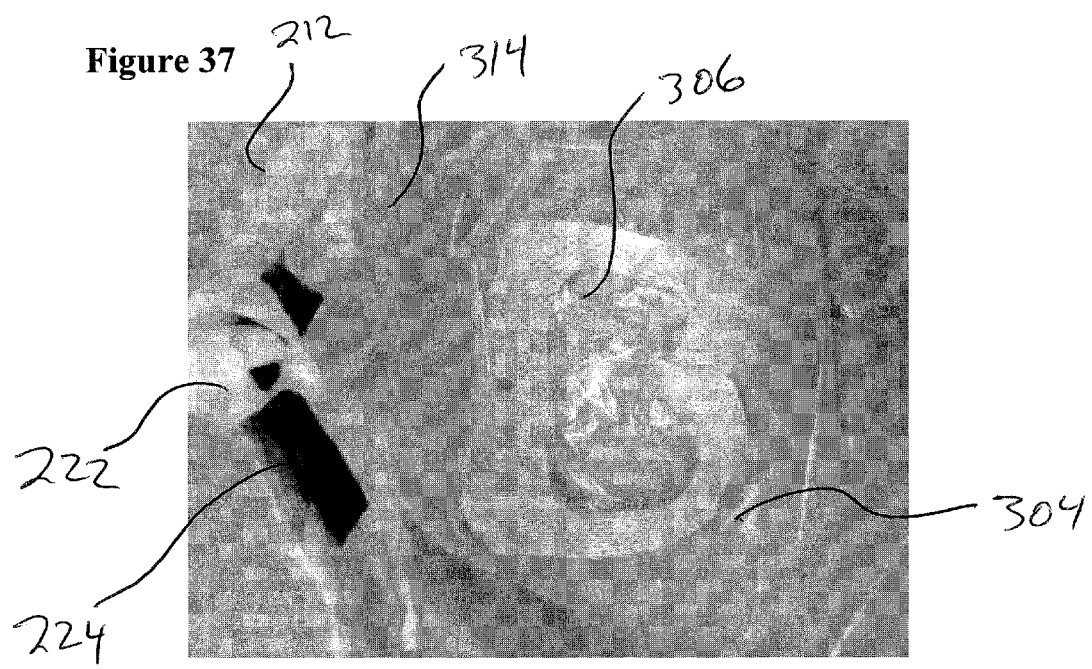
Figure 38:
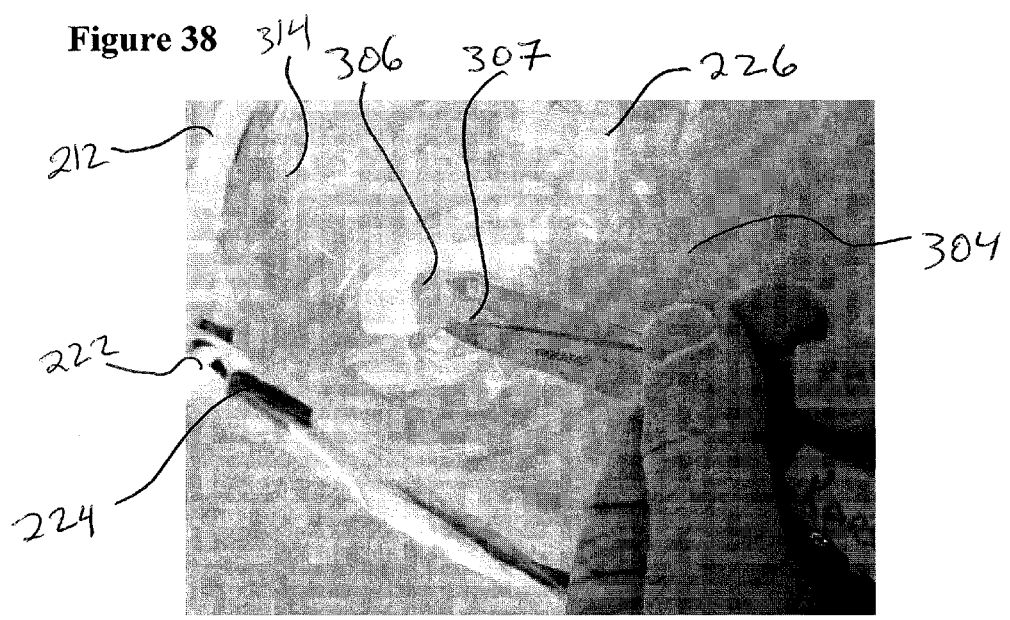
Figure 39:
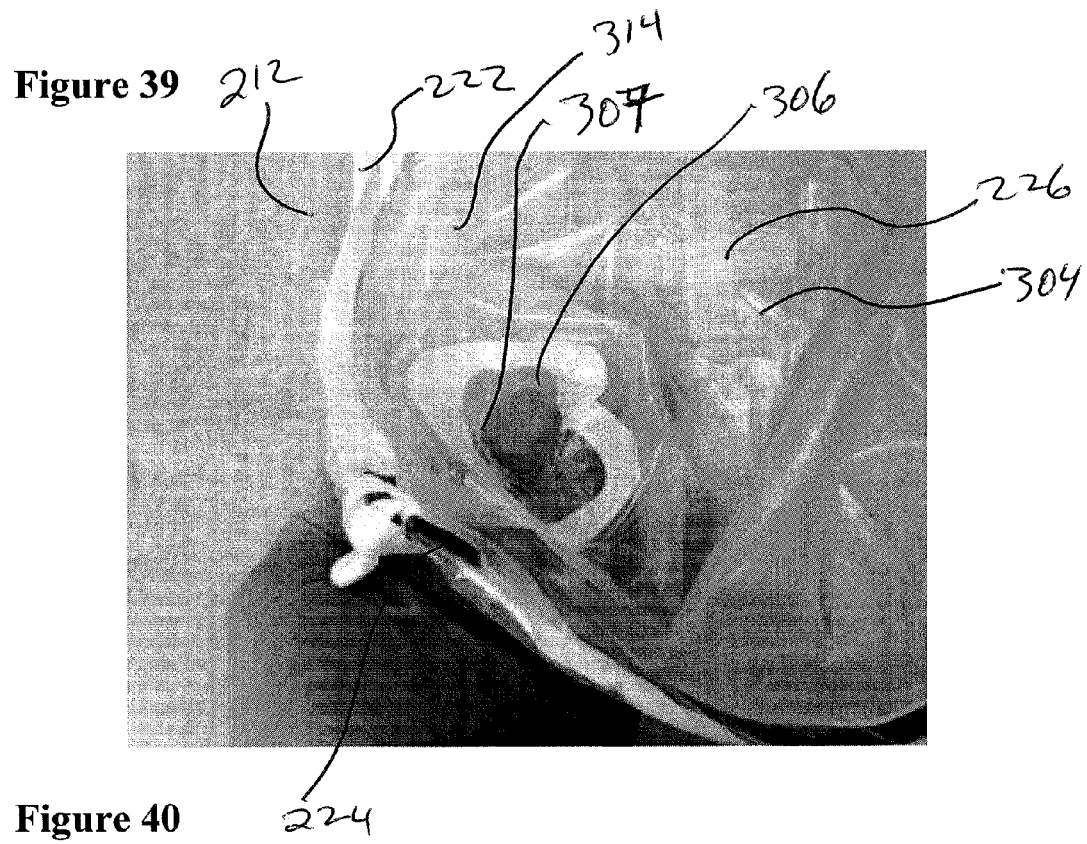
Figure 40:
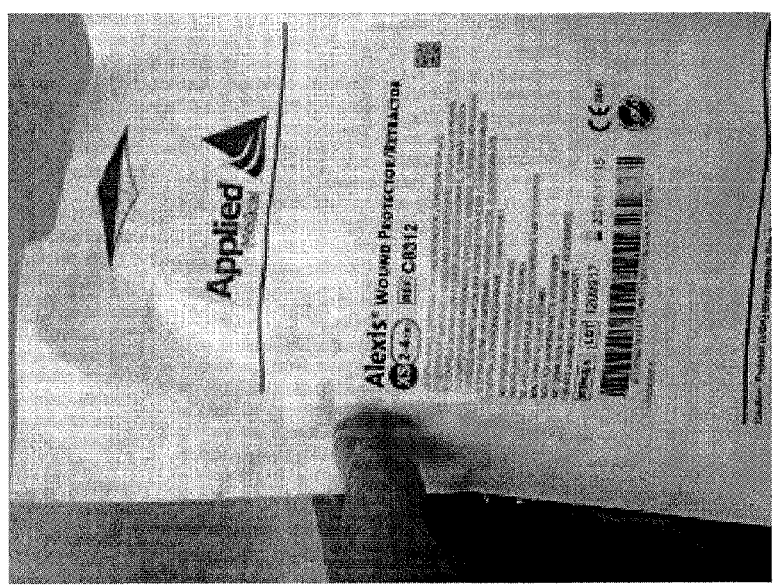
FIGS. 40, 41 and 42 show an embodiment of the sheath-like surgical communication (Alexis).
Figure 41:
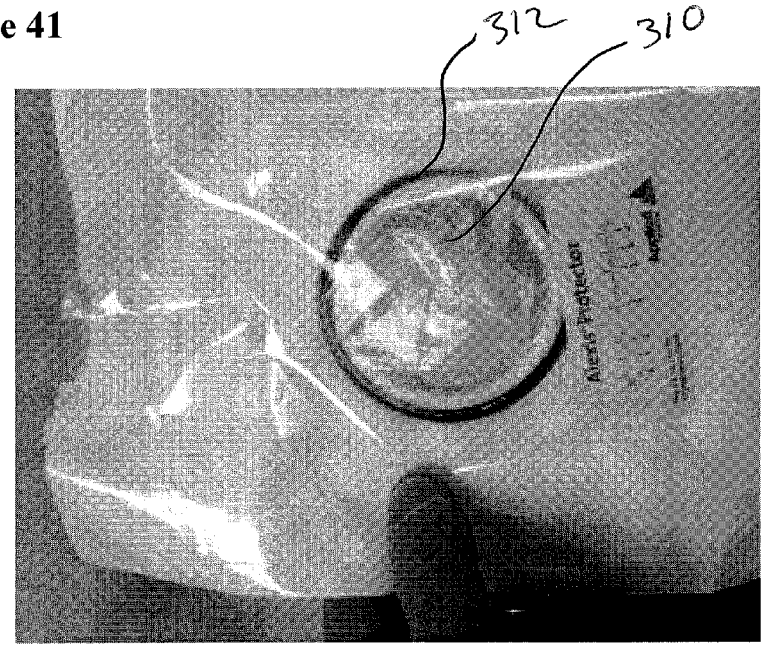
Figure 42:
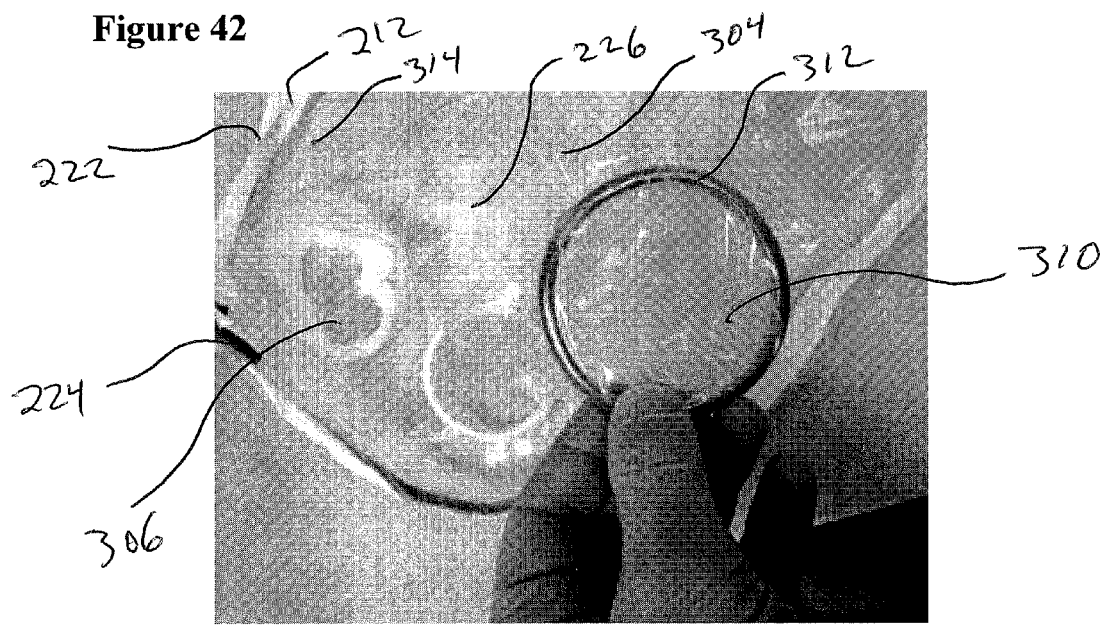
Figure 43:
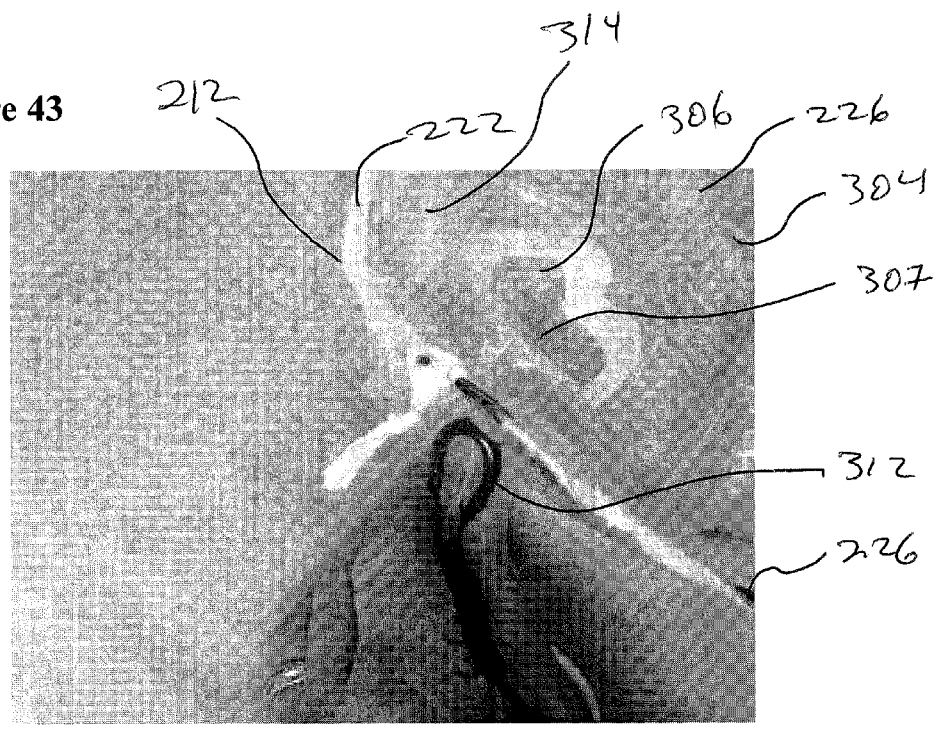
FIG. 43 shows the bendable O-ring of the sheath-like surgical communication being inserted through the communication in the bottom of the collection bag.
Figure 44:
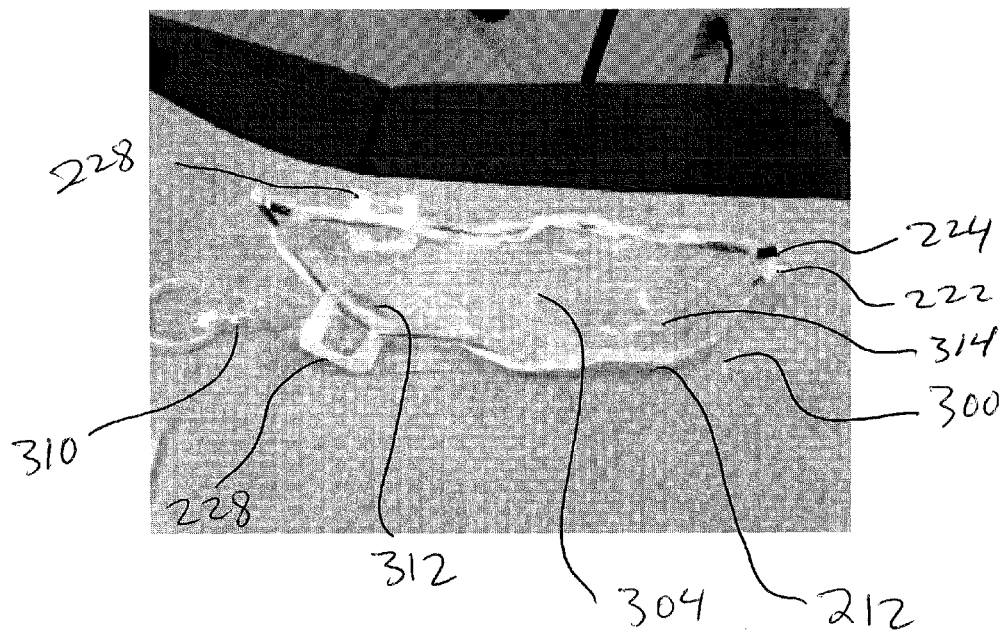
FIG. 44 shows a front perspective view of the transvaginal Endo-Field collection device of the present invention.
Figure 45:
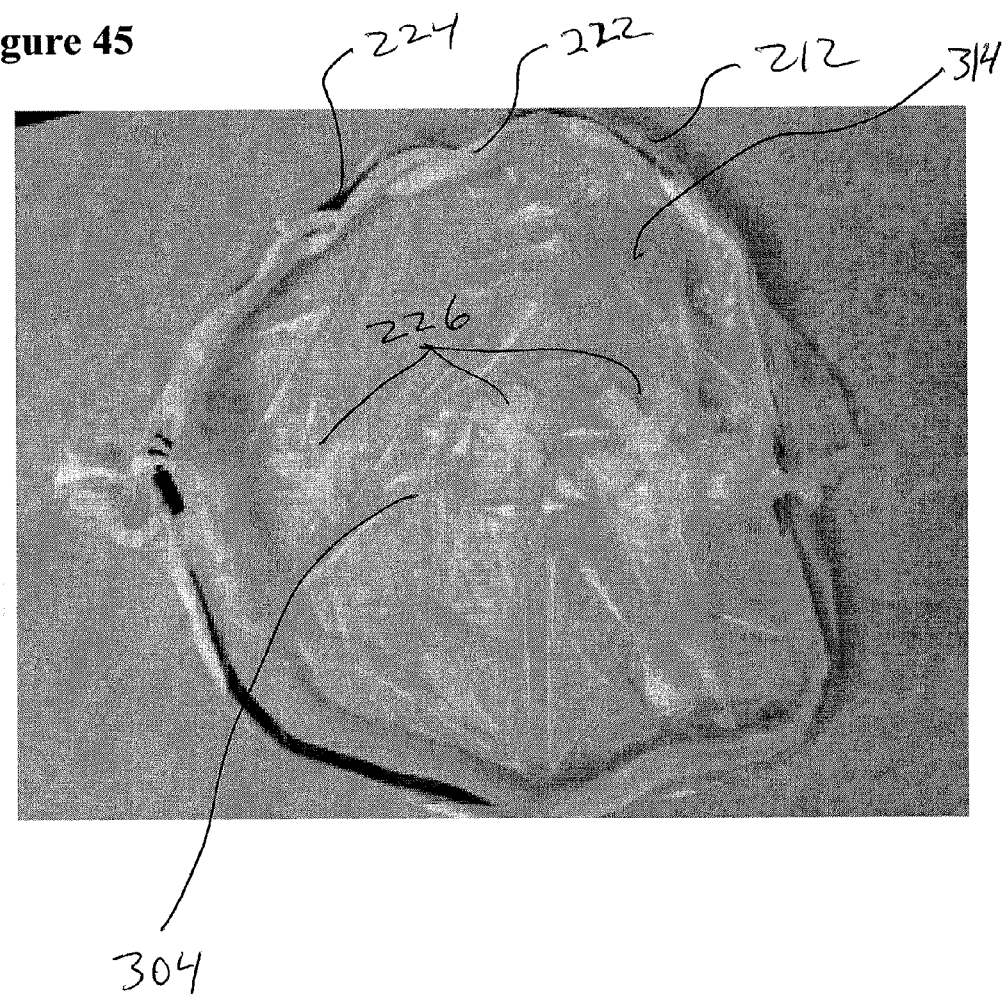
FIG. 45 shows a top view of the transvaginal Endo-Field collection device of the present invention.

Illustrative and alternative embodiments of the device 100 for collecting tissue, tissue debris, and blood, as well as methods of use thereof will be described in connection with FIGS. 1-45.

The term "collection device" is used generally to refer to the "Endo-Field collection device" 200 and the "Endo-Field TV collection device" 300.

The term "Endo-Field" is used generally to refer to the "device" and also the "collection device."

The term "Endo-Field TV" is used to refer to the Endo-Field collection device 200 that is modified to include a communication 302 (which may be reinforced with a sealable film) through the bottom 304 of the collection device 300 for use in transvaginal surgical procedures. The Endo-Field TV may also be adapted to include a surgical communication 308 positioned through and overlapping with the communication 302.

The terms "Morcellation," "laparoscopic," "laparoscopy," "hysterectomy," "myomectomy," and "trocar" are used in reference to their plain and ordinary meanings in the surgical art.

The terms "tissue," "blood," "skin," "peritoneal cavity," "vagina," and "cervix" are used in reference to their plain and ordinary meanings in the anatomical art.

The term "tissue debris" is used in reference to a piece(s) of tissue that may come dislodged, ripped, cut, or otherwise separated from a generally intact whole or partially intact organ, anatomical structure, or abnormal cancerous or non-cancerous growth(s) thereon. The piece(s) of tissue may be microscopic and/or macroscopic.

The invention provides a device 100 for collecting tissue, tissue debris, and blood that may become dislodged, separated, and/or sprayed during a surgical procedure, whether such procedure is laparoscopic or not. While exemplary embodiments of the invention are described in connection with procedures for Morcellation of the uterus, parts of the uterus, or abnormal cancerous or noncancerous growths thereof, these descriptions are non-limiting because the invention is also useful for other surgical procedures in which tissue, tissue debris, and/or blood may be dislodged, separated, and/or sprayed into an internal cavity during any surgical procedure.

A purpose of the invention is to provide a collection device 100 that may be used in connection with containing, collecting, and removing tissue, tissue debris, and blood that may become dislodged, separated, and/or sprayed during laparoscopy or other minimally invasive procedure. For example, the collection device 100 may be used with laparoscopic procedures in the peritoneal cavity, the cardiothoracic cavity including the pleural cavities, or other internal cavity of a human or animal body. More specifically, the collection device 100 may be used with surgical procedures in the peritoneal cavity that include, but are not limited to, hysterectomy (e.g., partial, total, or radical), myomectomy (fibroids), oophorectomy (unilateral or bilateral), salpingectomy (unilateral or bilateral), salpingo-oophorectomy (unilateral or bilateral), cystectomy, or other procedures to remove uterine tissue affected by endometriosis, intrauterine adhesions, pelvic inflammation, and the like. Furthermore, the collection device 100 may also be used with surgical procedures that include, but are not limited to, cholecystectomy, appendectomy, colectomy, pancreatectomy, liver resection, gastectomy, and the like. Alternatively, the collection device 100 may be used with surgical procedures in the pleural cavities including, but not limited to, lobectomy, wedge resection, segmental resection, and the like.

Another purpose of the invention is to provide a collection device 100 that can be collapsed and packed into a size and shape that can pass through a trocar or other opening placed in a manner to provide a passage into and out of an internal cavity of a human or animal such as, for example, the peritoneal cavity through the abdominal wall or the os of the cervix during surgery.

A further purpose of the invention is to provide a collection device 100 that can be easily deployed inside the peritoneal or other cavity in a human or animal during surgery in a manner that the device 100 is held open at its open end with flexible stays and maintains its general bag-like shape while deployed.

Yet another purpose of the invention is to provide a collection device 100 that functions as a protective barrier to a substantial portion of the parietal peritoneum and visceral peritoneum in the peritoneal cavity, or lining of other internal cavities of a human or animal during a surgical procedure.

An even further purpose of the invention is to provide a temporary basin in which to place an organ (such as the uterus) or portion thereof, or excised tissue from an organ or other anatomical body part of a human or animal, before and during Morcellation, laparoscopic, or other surgical procedure used to remove that organ or portion thereof, or excised tissue from a human or animal.

Yet an even further purpose of the invention is to provide a collection device 100 that is inexpensive and easy to manufacture.

Finally, another purpose of the invention is to provide a collection device 100 that is easy to train surgeons to use and does not stifle advances in laparoscopic surgery in humans or animals.

The Endo-Field collection device 200 (see FIG. 6) comprises a bag, basin, or other container structure having a closed bottom end 216 (or floor), an opened end 232 defined by an edge 212, and a wall(s) 214 configured between the closed bottom end 216 and the edge 212. The edge 212 (see FIGS. 11-13) may be defined by a folded over portion 218 of the wall(s) 214 that provide an internal channel 220 around the edge 212 of the bag, basin, or other container structure. In embodiments, a drawstring 222 (see FIGS. 11-13) may be provided within the internal channel 220, as well as one or more optional flexible stays 224 (see FIGS. 11-13).

In any configuration of the collection device 100, its components must allow the device 100 to be collapsed, rolled and/or folded into a shape and size that can pass through a trocar (15 mm, 12 mm, or other diameter) into and out of an internal cavity of a human or animal, the vagina/ cervix, or other communication into and out of an internal cavity of a human or animal, e.g., peritoneal cavity, pleural cavity, cardiothoracic cavity.

The bag, basin, or other container comprising the collection device 100 may comprise a flexible and/or malleable, and sufficiently strong, material that can withstand the physical stresses during passage through a trocar or other communication without tearing. The flexible material should provide a barrier to the passage of liquids. For example, this material may comprise a plastic or polymeric material or other material, or combination of materials, that provide similar characteristics. The flexibility and malleability of the material provides the collection device 100 with the ability to maintain a bag shape in a desired configuration when deployed during surgery since abdominal, pelvic, and specimen shapes and sizes vary from surgery to surgery. There are no limitations on size, shape, and volume of the collection device 100 other than that which is reasonable for the purposes of the invention. In an exemplary, but non-limiting, embodiment, the Endo-Field collection device 200 (see FIGS. 1, 14) comprises a depth (from the edge 212 to the bottom 216) of 8-inches, 6-inches, or other depth effective in meeting the purposes of the invention.

Drawstring 222 (see FIGS. 1, 6, 14) may be provided with the collection device 100. Drawstring 222 comprises at least one piece of string, mesh, rope, or other material. Drawstring 222 are provided to facilitate closure of the collection device 100 prior to its removal from the peritoneal cavity or other cavity during a surgical procedure, such as, for example during a hysterectomy.

In an alternative embodiment, flexible stays 224 (see FIGS. 15-18) may be provided with the collection device 100. Flexible stays 224 may comprise metal, plastic, or other flexible material, or a combination of metal, plastic, and/or flexible material capable of being positioned in a manner to maintain the open end of the collection device 100 in an open configuration.

In an optional embodiment, markings 226 (see FIGS. 1, 21-24) may be provided on the inside floor of the collection device 100. Markings 226 are provided as visual indicators useful for aiding in the spatial orientation of the inside and outside of the collection device 100 during use to prevent spillage of contents from the device 100. Markings 226 may be one or more SteriStrips (¼") adhered in an "X" pattern or other configuration at intervals along the inside surface 234 of the bottom 216 of the bag. In an embodiment, markings 226 may comprise tape having different colors on the exposed side and the adhesive side of the tape. In a specific embodiment, markings 226 comprise tape that has red on the adhesive side and green on the exposed side.

In another optional embodiment, tabs 228 (see FIG. 24) may be provided with the collection device 100. Tabs 228 may be configured in such a way that they rise above the edge 212 of the collection device 100 so that surgeons could sew, clamp, or otherwise temporarily attach the tabs 228 to the interior surface of the abdominal wall, thereby securing the collection device 100 in a desired position inside the peritoneal cavity for example. Tabs 228 may comprise sterile "rip-stop" plastic or other suitable material that can be attached to the external or internal surface of the collection device 100.

In yet another optional embodiment, the Endo-Field TV collection device 300 (see FIGS. 37-38, 43-45) is provided. It comprises the features, including any one or more optional features, of the Endo-Field collection device 200 configured with a communication 302 located through the bottom 304 of the device 300, and, in an embodiment, about one-third of the way across the bottom 304 from a wall 314. The Endo-Field TV collection device 300 may be assembled in a similar manner as the Endo-Field collection device 200 with the additional steps of adding communications 302, 307 and surgical communication 308. In an embodiment, communication 302 may be about a 5-15 mm expandable hole. Communication 302 (see FIGS. 37-40) may be reinforced with an expandable, re-sealable, self-healing, and/or flexible film 306 (Tegoderm film) or other material that is adhered over and around communication 302. Reinforcement material 306 also has a communication 307 that corresponds with communication 302 through the bottom 304 of the collection device 300 (see FIG. 39). Communication 307 in the reinforcement material 306 may be of a size that permits the passage of surgical tools, such as a trocar, morcellator, or other tool, from the outside to the inside of the Endo-Field TV collection device 300. Communication 307 of the reinforcement material 306 is also of a size that provides a tight seal with the surgical tool positioned within the communication 302 of the bottom 304 of the Endo-Field TV collection device 300; whereby, the seal prevents passage of tissue or fluids from inside the collection device 300. Reinforcement material 306 may also permit the communication 307 to close tightly with a water-tight seal to prevent leakage during and after removal of the surgical tool from the Endo-Field TV collection device 300 after desired tissue is removed during a procedure. Reinforcement film 306 will also close tightly to prevent leakage during and after removal of the surgical tool from the communication 302 in the bottom 304 of the Endo-Field TV collection device 300.

In a further embodiment of the Endo-Field TV collection device 300 (see FIGS. 25-26, 29-34), a surgical communication 308 may be provided relative to the communications 302, 307. Surgical communication 308 may comprise a cylindrical tube-like device 310 or other sheath-like device having two open ends. A flexible ring 312 integrated into the surgical communication 308 (see FIGS. 29-34) may be provided at a first open end of the surgical communication 308. In an exemplary embodiment, surgical communication 308 may comprise a surgical protector/retractor that provides 360° of circumferential, atraumatic retraction (e.g., Alexis wound protector/retractor, Applied Medical). The flexible ring 312 must be configured to permit it to pass through the communications 302, 307 of the Endo-Field TV collection device 300 and overlap with the reinforcement material 306 (see FIGS. 30-33).

All materials used to manufacture the collection device 100 must be capable of being sterilized for surgical use.

All embodiments of the collection device 100 may be commercially manufactured, sterilized, and hermitically sealed in a container. In alternative embodiments of the invention, the Endo-Field collection bag 200 (see FIG. 1) and the Endo-Field TV collection bag 300 (see FIG. 43) may also be manufactured from sterile components in an operating room prior to use in a surgical procedure.

In an exemplary embodiment of methods of manufacture, the Endo-Field collection bag 200 (see FIG. 1) can be created from a 20"×20" isolation bag (3M Steri-Drape) or other suitably-sized, sterilized bag (see FIGS. 2-23). The drawstring 222 must be removed and saved for later use (see FIG. 5) with the collection bag 200. Then, the isolation bag can be cut to a desired height from the bottom closed portion of the bag (see FIGS. 3-4). In non-limiting examples, this height can be 6" to 8" from the bottom closed end 216 of the isolation bag. The upper edge 230 of the bag 210 (the edge that was cut) must be folded over to overlap with the walls 214 of the bag 210 (see FIGS. 9-13). The previously-removed drawstring 222 should be positioned within the overlapping region of the bag 210 (see FIG. 9). The overlap 218 must then be taped (3M Steri-Drape Incise Drape 1040) (see FIGS. 10-13) or sealed to the outside surface of the bag 210 to create channels 220 around the upper edge 212 of the bag 210 that hold the drawstring 222 in place around the periphery of open end 232. In an embodiment, the fold 218 may be about 1 to 1½ inches (see FIG. 8).

Flexible stays 225 may be provided, such as, for example, as blue support rails cut from support rails of a sterile robotic drape used to cover the patient during surgery (see FIGS. 15-18). The flexible stays 225 are fed into the channels 220 alongside optional drawstrings 222, and the ends of the flexible stays 225 can be folded over so that the folded ends are positioned inside the channels 220 as a safety precaution to prevent "hooking" onto the trocar and/or tissue during insertion and removal of the Endo-Field collection device 200.

Markings 226 may be provided on the inside surface 234 of the bottom 216 of the Endo-Field collection bag 200 (see FIGS. 20-23).

Tabs 228 may be provided as sterile "rip-stop" plastic attached to the external or internal surface of the Endo-Field collection bag 200 (see FIG. 24) and extend above the upper edge 212 at a distance, such as, for example, an inch, so that the tabs 228 can be sutured, clamped, or otherwise attached to the surface of the peritoneal cavity.

Methods of using the Endo-Field collection device 200 are provided. A sterile Endo-Field collection device 200 is either rolled or folded along its longest edge so that the rolled or folded Endo-Field collection device 200 can pass through a trocar (15 mm, 12 mm, or other size) providing a communication into and out of an internal cavity of a human or animal. For example, the trocar could be placed through a patient's abdominal wall into the peritoneal cavity, which may have positive air pressure placed in it to distend the abdomen with air to provide an open space in the peritoneal cavity in which to perform the surgical procedure. Other trocars or surgical communications may also be used to provide access for surgical tools/devices that are necessary to perform the surgical procedure within an internal cavity of a human or animal.

If a hysterectomy is being performed, the uterus is removed from the cervix with a surgical cautery device or other cutting device at the cervical stump or other location around the cervix. If a myomectomy or other tissue excise procedure is being performed, e.g., oophorectomy, salpingectomy, salpingo-oophorectomy, cystectomy, tissue effected by endometriosis, intrauterine adhesions, pelvic inflammation, and the like, cholecystectomy, appendectomy, colectomy, pancreatectomy, liver resection, gastectomy, and the like, the target tissue may be removed from the organ or body part with a surgical cautery device or other cutting device. The Endo-Field collection device 200 can be inserted into the peritoneal cavity through the trocar before or after the uterus is separated from the cervix, or the fibroid or tissue is excised from the uterus.

The Endo-Field collection device 200 is then deployed internally within the peritoneal cavity. Laparoscopic or other grippers may be used to unroll/unfold the Endo-Field collection device 200 and then place the open Endo-Field collection device 200 in a position in the peritoneal cavity that substantially covers a significant portion of the peritoneal cavity.

This position should also maximize collection of blood and tissue that may spray or drop from the uterus during Morcellation or other tissue extraction procedure. The optional flexible stays 224 are used to maintain the Endo-Field collection device 200 in the desired open position. If present, tabs 228 may be used with grippers or another device to anchor the Endo-Field collection device 200 to the wall of the peritoneal cavity.

With the Endo-Field collection device 200 positioned in a desired location in the peritoneal cavity, the next step is to place the uterus (if cut free from the cervix and other surrounding connective tissue for hysterectomy), fibroid(s) (with or without the uterus for a myomectomy), or other excised tissue inside the collection device 200 and substantially resting on the interior surface of the bottom 216 of the bag 210, and then use a Morcellation device or other tool or device used to remove the uterus, the fibroid(s), or other excised tissue from the peritoneal cavity. Blood and tissue that may fall or spray from the uterus during Morcellation is collected in the Endo-Field collection device 200 that functions also as a protective barrier, and then the blood and tissue resting in the Endo-Field collection device 200 is later substantially removed from the peritoneal cavity using the Morcellator, suction device, or other surgical device. Finally, the Endo-Field collection device 200 is removed from the peritoneal cavity by using surgical grippers to grip the collection device and then to pull it out of the peritoneal cavity through the trocar, with particular attention paid to maintaining any residual tissue or blood inside the collection device 200.

The cut or cauterized cervix (hysterectomy) or portion of the uterus (myomectomy) may then be sutured and/or contacted with an absorbable hemostat material (e.g., structured non-woven material (SNoW)—Ethicon). Then, an adhesion barrier (Gynecare INTERCEED—Ethicon) may be placed over the cut or cauterized surface of the cervix or uterus in order to prevent excessive scar tissue formation and/or adhesion of the cut or cauterized surface to internal organs.

Of course, the aforementioned examples of the methods are exemplary only. The collective device can be used in connection laparoscopic procedures used to remove organ or tissue from any internal cavities of a human or animal.

Methods of using an Endo-Field TV collection device 300 are also provided. A sterile Endo-Field TV collection device 300 (without a surgical communication 308 connected thereto) is either rolled or folded along its longest edge so that the rolled or folded Endo-Field collection device 300 can pass through a trocar (15 mm, 12 mm, or other size). Positive air pressure is placed in the peritoneal cavity to distend the abdomen with air to provide an open space in the peritoneal cavity in which to perform the procedure. Using a surgical cautery device or other cutting device, the uterus may be removed along with a portion of the cervix at the cervical stump or other location around the cervix. The Endo-Field TV collection device 300 (without a surgical communication 308 connected thereto) can be placed into the peritoneal cavity through a trocar positioned through the os of the cervix (with uterus removed), or, alternatively, the Endo-Field TV collection device 300 (without a surgical communication 308 connected thereto) can be passed into the peritoneal cavity through a trocar in the abdominal wall either before or after the uterus is separated from the cervix.

The Endo-Field TV collection device 300 is then deployed internally within the peritoneal cavity in a similar manner as the Endo-Field collection device 200 using laparoscopic or other grippers to unroll/unfold the Endo-Field TV collection device 300 and then place the open Endo-Field TV collection device 300 in position in the peritoneal cavity that substantially covers a significant portion of the peritoneal cavity. Flexible stays 224 can be used to maintain the Endo-Field TV collection device 300 in a desired open position. If present, tabs 228 may be used with grippers or other devices to anchor the Endo-Field TV collection device 300 to the wall of the peritoneal cavity.

The communications 302, 307 of the Endo-Field TV collection device 300 is positioned over the cervix. A trocar (15 mm, 12 mm, or other size) may be inserted through the os of the cervix and the communications 302, 307 into the peritoneal cavity. In an embodiment, a Morcellation device is passed through the trocar and communications 302, 307 into the Endo-Field TV communication device 300 with reinforcement film 306 that forms a seal with the Morcellation device.

In an alternative embodiment, the flexible ring 312 of a surgical communication 308 (e.g., Alexis wound protector/retractor, Applied Medical) is passed through the os of the cervix and the communications 302, 307 into the Endo-Field TV collection device 300. The flexible ring 312 is positioned against the inner surface of the Endo-Field TV collection device 300 such that it is fully expanded into its ring shape. The other end of the surgical communication 308 (inside or outside of the vagina) is pulled so that the end of the surgical communication 308 with the flexible ring 312 is resting tightly on top of, and overlapping well beyond, the communications 302, 307 of the Endo-Field TV collection device 300. This configuration creates a seal between the surgical communications 302, 307 and the bottom 216 of the Endo-Field TV collection device 300.

With the Endo-Field TV collection device 300 positioned in a desired location in the peritoneal cavity, the next step is to place the uterus in the collection device 300 and then use a morcellator (Ethicon) inserted through the surgical communication 308 into the peritoneal cavity to remove the uterus. During Morcellation, blood and tissue that may fall or spray from the morcellator is collected in the Endo-Field TV collection device 300, and then the blood and tissue resting in the Endo-Field TV collection device 300 is later removed from the peritoneal cavity using the Morcellator, suction device, and/or other surgical device. Finally, the Endo-Field TV collection device 300 is removed from the peritoneal cavity by pulling the surgical communication 308 and the Endo-Field TV collection device 300 through the os of the cervix and out of the vagina.

Alternatively, the surgical communication 308 can be removed through the os of the cervix and the vagina, while the Endo-Field TV collection device 300 is removed through a trocar positioned through the abdominal wall or in the os of the cervix. The cut or cauterized cervix may be sutured and/or contacted with an absorbable hemostat material (structured non-woven material (SNoW)—Ethicon). An adhesion barrier (Gynecare INTERCEED—Ethicon) may also be placed over the cauterized surface of the cervix in order to prevent excessive scar tissue formation and/or adhesion of the cut or cauterized surface to internal organs.

Throughout all procedures in which the collection device 100 is being used, the surgeon and assistants should implement measures to maintain a sterile field while observing the surgical aseptic technique.

While the invention is described in conjunction with specific embodiments, many alternatives, modifications, permutations, and variations will become apparent to those skilled in the art in light of the foregoing description. Accordingly, it is intended that the invention embraces all such alternatives, modifications, permutations, and variations as falling within the scope of the claims below.

We claim:

1. A bag to collect tissue debris and blood during a surgical procedure comprising:
   a collapsible, protective barrier comprising a closed bottom, an open edge, and wall between said closed bottom and said open end;
   at least one stay provided adjacent said open edge and configured maintain a shape; and
   at least one tab comprising a rigid and flexible material secured adjacent to said open edge;
   wherein the height of the bag is less than or equal to half the width of the bag;
   wherein said bag is configured when collapsed to pass through a trocar into a peritoneal cavity and then deployed within said peritoneal cavity to form a temporary basin in which tissue may be placed or blood or tissue parts collected.

2. The bag of claim 1 comprising at least one marker provided on an inner surface of said closed bottom.

3. The bag of claim 1 comprising a channel provided around said edge of said barrier.

4. The bag of claim 3 wherein said at least one stay or a drawstring is provided within said channel.

5. The bag of claim 1 comprising a cylindrical sheath having a first open end, a second open end, and a flexible O-ring integrated into said first open end.

6. The bag of claim 5 wherein said closed bottom comprises a communication through which said flexible O-ring can pass through.

* * * * *